US007115560B2

(12) United States Patent
Zhou

(10) Patent No.: US 7,115,560 B2
(45) Date of Patent: Oct. 3, 2006

(54) METHODS FOR MODULATING GASTRIC SECRETION USING PROKINETICIN RECEPTOR ANTAGONISTS

(75) Inventor: Qun-Yong Zhou, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 131 days.

(21) Appl. No.: 10/811,328

(22) Filed: Mar. 25, 2004

(65) Prior Publication Data

US 2005/0026828 A1 Feb. 3, 2005

Related U.S. Application Data

(60) Provisional application No. 60/457,891, filed on Mar. 25, 2003.

(51) Int. Cl.
*C07K 14/00* (2006.01)
(52) U.S. Cl. .......................... 514/2; 530/300; 530/350

(58) Field of Classification Search ................ 514/2; 530/300, 350
See application file for complete search history.

*Primary Examiner*—Karen Cochrane Carlson
(74) *Attorney, Agent, or Firm*—DLA Piper Rudnick Gray Cary US LLP

(57) ABSTRACT

The invention provides methods of modulating gastric acid secretion by administering an amount of a prokineticin receptor antagonist effective to alter one or more indicia of gastric acid secretion, wherein the antagonist contains an amino acid sequence at least 80% identical to amino acids to 7 to 77 of SEQ ID NO:3, which includes (a) the 10 conserved cysteine residues of SEQ ID NO:3, and (b) from 0 to 9 of amino acids 78 to 86 of SEQ ID NO:3, wherein amino acids 1 to 6 of the antagonist do not consist of amino acids AVITGA (SEQ ID NO:21). In another embodiment, the antagonist contains an amino acid sequence at least 80% identical to amino acids to 7 to 77 of SEQ ID NO:6, which includes (a) the 10 conserved cysteine residues of SEQ ID NO:6, and (b) from 0 to 4 of amino acids 78 to 81 of SEQ ID NO:6, wherein amino acids 1 to 6 of the antagonist do not consist of amino acids AVITGA (SEQ ID NO:21).

39 Claims, 10 Drawing Sheets

SEQUENCE LISTING

<160> NUMBER OF SEQ ID NOS: 32

<210> SEQ ID NO 1
<211> LENGTH: 1377
<212> TYPE: DNA
<213> ORGANISM: Homo sapiens
<220> FEATURE:
<221> NAME/KEY: CDS
<222> LOCATION: (55)...(369)

<400> SEQUENCE: 1

```
ggggaagcga gaggcatcta agcaggcagt gttttgcctt cacccccaagt gacc atg       57
                                                             Met
                                                             1 aga ggt gcc acg cga gtc tca atc atg ctc ctc cta gta act gtg tct       105
Arg Gly Ala Thr Arg Val Ser Ile Met Leu Leu Leu Val Thr Val Ser
        5                  10                  15 gac tgt gct gtg atc aca ggg gcc tgt gag cgg gat gtc cag tgt ggg       153
Asp Cys Ala Val Ile Thr Gly Ala Cys Glu Arg Asp Val Gln Cys Gly
            20                  25                  30 gca ggc acc tgc tgt gcc atc agc ctg tgg ctt cga ggg ctg cgg atg       201
Ala Gly Thr Cys Cys Ala Ile Ser Leu Trp Leu Arg Gly Leu Arg Met
 35                  40                  45 tgc acc ccg ctg ggg cgg gaa ggc gag gag tgc cac ccc ggc agc cac       249
Cys Thr Pro Leu Gly Arg Glu Gly Glu Glu Cys His Pro Gly Ser His
 50                  55                  60                  65 aag gtc ccc ttc ttc agg aaa cgc aag cac cac acc tgt cct tgc ttg       297
Lys Val Pro Phe Phe Arg Lys Arg Lys His His Thr Cys Pro Cys Leu
                 70                  75                  80 ccc aac ctg ctg tgc tcc agg ttc ccg gac ggc agg tac cgc tgc tcc       345
Pro Asn Leu Leu Cys Ser Arg Phe Pro Asp Gly Arg Tyr Arg Cys Ser
             85                  90                  95 atg gac ttg aag aac atc aat ttt taggcgcttg cctggtctca ggatacccac     399
Met Asp Leu Lys Asn Ile Asn Phe
         100                 105 catccttttc tgagcacagc ctggattttt atttctgcca tgaaacccag ctcccatgac    459
tctcccagtc cctacactga ctaccctgat ctctcttgtc tagtacgcac atatgcacac    519
aggcagacat acctcccatc atgacatggt ccccaggctg gcctgaggat gtcacagctt    579
gaggctgtgg tgtgaaaggt ggccagcctg gttctcttcc ctgctcaggc tgccagagag    639
gtggtaaatg gcagaaagga cattcccct ccctccccca ggtgacctgc tctctttcct    699
gggccctgcc cctctcccca catgtatccc tcggtctgaa ttagacattc ctgggcacag    759
gctcttgggt gcattgctca gagtcccagg tcctggcctg accctcaggc ccttcacgtg    819
aggtctgtga ggaccaattt gtgggtagtt catcttccct cgattggtta actccttagt    879
ttcagaccac agactcaaga ttggctcttc ccagagggca gcagacagtc accccaaggc    939
aggtgtaggg agcccaggga ggccaatcag cccctgaag actctggtcc cagtcagcct     999
gtggcttgtg gcctgtgacc tgtgaccttc tgccagaatt gtcatgcctc tgaggccccc   1059
tcttaccaca ctttaccagt taaccactga agccccccaat tcccacagct tttccattaa   1119
aatgcaaatg gtggtggttc aatctaatct gatattgaca tattgaaagg caattagggt   1179
gtttccttaa caactccttt tccaaggatc agccctgaga gcaggttggt gactttgagg   1239
agggcagtcc tctgtccaga ttggggtggg agcaagggac agggagcagg gcaggggctg   1299 aaagggcac tgattcagac cagggaggca actacacacc aacctgctgg ctttagaata   1359
```
aaagcaccaa ctgaactg                                                    1377

<210> SEQ ID NO 2
<211> LENGTH: 105
<212> TYPE: PRT
<213> ORGANISM: Homo sapiens

<400> SEQUENCE: 2

Met Arg Gly Ala Thr Arg Val Ser Ile Met Leu Leu Val Thr Val
1               5                   10                  15

Ser Asp Cys Ala Val Ile Thr Gly Ala Cys Glu Arg Asp Val Gln Cys
            20                  25                  30

Gly Ala Gly Thr Cys Cys Ala Ile Ser Leu Trp Leu Arg Gly Leu Arg
        35                  40                  45

Met Cys Thr Pro Leu Gly Arg Glu Gly Glu Cys His Pro Gly Ser
    50                  55                  60

His Lys Val Pro Phe Phe Arg Lys Arg Lys His His Thr Cys Pro Cys
65                  70                  75                  80

Leu Pro Asn Leu Leu Cys Ser Arg Phe Pro Asp Gly Arg Tyr Arg Cys
                85                  90                  95

Ser Met Asp Leu Lys Asn Ile Asn Phe
            100                 105

<210> SEQ ID NO 3
<211> LENGTH: 86
<212> TYPE: PRT
<213> ORGANISM: Homo sapiens

<400> SEQUENCE: 3

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
            20                  25                  30

Pro Leu Gly Arg Glu Gly Glu Cys His Pro Gly Ser His Lys Val
        35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys Asn Ile Asn Phe
                85

<210> SEQ ID NO 4
<211> LENGTH: 1406
<212> TYPE: DNA
<213> ORGANISM: Homo sapiens
<220> FEATURE:
<221> NAME/KEY: CDS
<222> LOCATION: (10)...(333)

<400> SEQUENCE: 4 gagggcgcc atg agg agc ctg tgc tgc gcc cca ctc ctg ctc ctc ttg ctg    51
          Met Arg Ser Leu Cys Cys Ala Pro Leu Leu Leu Leu Leu Leu
          1               5                   10 ctg ccg ccg ctg ctg ctc acg ccc cgc gct ggg gac gcc gcc gtg atc    99
Leu Pro Pro Leu Leu Leu Thr Pro Arg Ala Gly Asp Ala Ala Val Ile
15                  20                  25                  30 acc ggg gct tgt gac aag gac tcc caa tgt ggt gga ggc atg tgc tgt   147
Thr Gly Ala Cys Asp Lys Asp Ser Gln Cys Gly Gly Gly Met Cys Cys
                35                  40                  45

```
gct gtc agt atc tgg gtc aag agc ata agg att tgc aca cct atg ggc      195
Ala Val Ser Ile Trp Val Lys Ser Ile Arg Ile Cys Thr Pro Met Gly
         50                  55                  60 aaa ctg gga gac agc tgc cat cca ctg act cgt aaa gtt cca ttt ttt      243
Lys Leu Gly Asp Ser Cys His Pro Leu Thr Arg Lys Val Pro Phe Phe
 65                  70                  75 ggg cgg agg atg cat cac act tgc cca tgt ctg cca ggc ttg gcc tgt      291
Gly Arg Arg Met His His Thr Cys Pro Cys Leu Pro Gly Leu Ala Cys
     80                  85                  90 tta cgg act tca ttt aac cga ttt att tgt tta gcc caa aag              333
Leu Arg Thr Ser Phe Asn Arg Phe Ile Cys Leu Ala Gln Lys
 95                 100                 105 taatcgctct ggagtagaaa ccaaatgtga atagccacat cttacctgta aagtcttact    393
tgtgattgtg ccaaacaaaa aatgtgccag aaagaaatgc tcttgcttcc tcaactttcc    453
aagtaacatt tttatctttg atttgtaaat gattttttttt tttttttttta tcgaaagaga  513
attttacttt tggatagaaa tatgaagtgt aaggcattat ggaactggtt cttatttccc    573
tgtttgtgtt ttggtttgat ttggcttttt tcttaaatgt caaaaacgta cccatttttca   633
caaaaatgag gaaataaga atttgatatt ttgttagaaa aacttttttt ttttttctc      693
accaccccaa gccccatttg tgccctgccg cacaaataca cctacagctt ttggtccctt    753
gcctcttcca cctcaaagaa tttcaaggct cttaccttac tttattttttg tccatttctc   813
ttccctcctc ttgcatttta aagtggaggg tttgtctctt tgagtttgat ggcagaatca    873
ctgatgggaa tccagctttt tgctggcatt taaatagtga aaagagtgta tatgtgaact    933
tgacactcca aactcctgtc atggcacgga agctaggagt gctgctggac ccttcctaaa    993
cctgtcactc aagaggactt cagctctgct gttgggctgg tgtgtggaca gaaggaatgg    1053
aaagccaaat taatttagtc cagatttcta ggtttgggtt tttctaaaaa taaaagatta    1113
catttacttc ttttactttt tataaagttt ttttttcctta gtctcctact tagagatatt   1173
ctagaaaatg tcacttgaag aggaagtatt tattttaatc tggcacaaca ctaattacca    1233
ttttttaaagc ggtattaagt tgtaatttaa accttgtttg taactgaaag gtcgattgta   1293
atggattgcc gtttgtacct gtatcagtat tgctgtgtaa aaattctgta tcagaataat    1353
aacagtactg tatatcattt gatttatttt aatattatat ccttattttt gtc           1406
```

<210> SEQ ID NO 5
<211> LENGTH: 108
<212> TYPE: PRT
<213> ORGANISM: Homo sapiens

<400> SEQUENCE: 5

```
Met Arg Ser Leu Cys Cys Ala Pro Leu Leu Leu Leu Leu Leu Leu Pro
 1               5                  10                  15

Pro Leu Leu Leu Thr Pro Arg Ala Gly Asp Ala Ala Val Ile Thr Gly
                 20                  25                  30

Ala Cys Asp Lys Asp Ser Gln Cys Gly Gly Met Cys Cys Ala Val
             35                  40                  45

Ser Ile Trp Val Lys Ser Ile Arg Ile Cys Thr Pro Met Gly Lys Leu
 50                  55                  60

Gly Asp Ser Cys His Pro Leu Thr Arg Lys Val Pro Phe Phe Gly Arg
 65                  70                  75                  80

Arg Met His His Thr Cys Pro Cys Leu Pro Gly Leu Ala Cys Leu Arg
                 85                  90                  95
```

```
Thr Ser Phe Asn Arg Phe Ile Cys Leu Ala Gln Lys
            100                 105

<210> SEQ ID NO 6
<211> LENGTH: 81
<212> TYPE: PRT
<213> ORGANISM: Homo sapiens

<400> SEQUENCE: 6

Ala Val Ile Thr Gly Ala Cys Asp Lys Asp Ser Gln Cys Gly Gly Gly
  1               5                  10                  15

Met Cys Cys Ala Val Ser Ile Trp Val Lys Ser Ile Arg Ile Cys Thr
             20                  25                  30

Pro Met Gly Lys Leu Gly Asp Ser Cys His Pro Leu Thr Arg Lys Val
         35                  40                  45

Pro Phe Phe Gly Arg Arg Met His His Thr Cys Pro Cys Leu Pro Gly
     50                  55                  60

Leu Ala Cys Leu Arg Thr Ser Phe Asn Arg Phe Ile Cys Leu Ala Gln
 65                  70                  75                  80

Lys

<210> SEQ ID NO 7
<211> LENGTH: 21
<212> TYPE: PRT
<213> ORGANISM: Homo sapiens

<400> SEQUENCE: 7

Asn Asn Phe Gly Asn Gly Arg Gln Glu Arg Lys Arg Lys Arg Ser
  1               5                  10                  15

Lys Arg Lys Lys Glu
             20

<210> SEQ ID NO 8
<211> LENGTH: 21
<212> TYPE: PRT
<213> ORGANISM: Homo sapiens

<400> SEQUENCE: 8

Ser His Val Ala Asn Gly Arg Gln Glu Arg Arg Ala Lys Arg Arg
  1               5                  10                  15

Lys Arg Lys Lys Glu
             20

<210> SEQ ID NO 9
<211> LENGTH: 19
<212> TYPE: PRT
<213> ORGANISM: Homo sapiens

<400> SEQUENCE: 9

Met Arg Gly Ala Thr Arg Val Ser Ile Met Leu Leu Leu Val Thr Val
  1               5                  10                  15

Ser Asp Cys

<210> SEQ ID NO 10
<211> LENGTH: 26
<212> TYPE: PRT
<213> ORGANISM: Homo sapiens

<400> SEQUENCE: 10

Met Arg Ser Leu Cys Cys Ala Pro Leu Leu Leu Leu Leu Leu Leu Pro
  1               5                  10                  15
```

```
Leu Leu Leu Thr Pro Ala Gly Asp Ala
            20              25

<210> SEQ ID NO 11
<211> LENGTH: 96
<212> TYPE: PRT
<213> ORGANISM: Bombina variegata

<400> SEQUENCE: 11

Met Lys Cys Phe Ala Gln Ile Val Val Leu Leu Val Ile Ala Phe
1               5                   10                  15

Ser His Gly Ala Val Ile Thr Gly Ala Cys Asp Lys Asp Val Gln Cys
            20                  25                  30

Gly Ser Gly Thr Cys Cys Ala Ala Ser Ala Trp Ser Arg Asn Ile Arg
            35                  40                  45

Phe Cys Ile Pro Leu Gly Asn Ser Gly Glu Asp Cys His Pro Ala Ser
        50                  55                  60

His Lys Val Pro Tyr Asp Gly Lys Arg Leu Ser Ser Leu Cys Pro Cys
65                  70                  75                  80

Lys Ser Gly Leu Thr Cys Ser Lys Ser Gly Glu Lys Phe Lys Cys Ser
                85                  90                  95

<210> SEQ ID NO 12
<211> LENGTH: 81
<212> TYPE: PRT
<213> ORGANISM: Dendroaspis polylepis polylepis

<400> SEQUENCE: 12

Ala Val Ile Thr Gly Ala Cys Glu Arg Asp Leu Gln Cys Gly Lys Gly
1               5                   10                  15

Thr Cys Cys Ala Val Ser Leu Trp Ile Lys Ser Val Arg Val Cys Thr
            20                  25                  30

Pro Val Gly Thr Ser Gly Glu Asp Cys His Pro Ala Ser His Lys Ile
            35                  40                  45

Pro Phe Ser Gly Gln Arg Lys Met His His Thr Cys Pro Cys Ala Pro
        50                  55                  60

Asn Leu Ala Cys Val Gln Thr Ser Pro Lys Lys Phe Lys Cys Leu Ser
65                  70                  75                  80

Lys

<210> SEQ ID NO 13
<211> LENGTH: 81
<212> TYPE: PRT
<213> ORGANISM: Artificial Sequence
<220> FEATURE:
<223> OTHER INFORMATION: synthetic construct

<400> SEQUENCE: 13

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Val
            35                  40                  45

Pro Phe Phe Gly Arg Arg Met His His Thr Cys Pro Cys Leu Pro Gly
        50                  55                  60

Leu Ala Cys Leu Arg Thr Ser Phe Asn Arg Phe Ile Cys Leu Ala Gln
65                  70                  75                  80
```

```
<210> SEQ ID NO 14
<211> LENGTH: 86
<212> TYPE: PRT
<213> ORGANISM: Artificial Sequence
<220> FEATURE:
<223> OTHER INFORMATION: synthetic construct

<400> SEQUENCE: 14

Ala Val Ile Thr Gly Ala Cys Asp Lys Asp Ser Gln Cys Gly Gly
 1               5                  10                  15

Met Cys Cys Ala Val Ser Ile Trp Val Lys Ser Ile Arg Ile Cys Thr
                20                  25                  30

Pro Met Gly Lys Leu Gly Asp Ser Cys His Pro Leu Thr Arg Lys Val
            35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys Asn Ile Asn Phe
                85

<210> SEQ ID NO 15
<211> LENGTH: 89
<212> TYPE: PRT
<213> ORGANISM: Artificial Sequence
<220> FEATURE:
<223> OTHER INFORMATION: synthetic construct

<400> SEQUENCE: 15

Gly Ile Leu Ala Val Ile Thr Gly Ala Cys Glu Arg Asp Val Gln Cys
 1               5                  10                  15

Gly Ala Gly Thr Cys Cys Ala Ile Ser Leu Trp Leu Arg Gly Leu Arg
                20                  25                  30

Met Cys Thr Pro Leu Gly Arg Glu Gly Glu Glu Cys His Pro Gly Ser
            35                  40                  45

His Lys Val Pro Phe Phe Arg Lys Arg Lys His His Thr Cys Pro Cys
    50                  55                  60

Leu Pro Asn Leu Leu Cys Ser Arg Phe Pro Asp Gly Arg Tyr Arg Cys
65                  70                  75                  80

Ser Met Asp Leu Lys Asn Ile Asn Phe
                85

<210> SEQ ID NO 16
<211> LENGTH: 85
<212> TYPE: PRT
<213> ORGANISM: Artificial Sequence
<220> FEATURE:
<223> OTHER INFORMATION: synthetic construct

<400> SEQUENCE: 16

Val Ile Thr Gly Ala Cys Glu Arg Asp Val Gln Cys Gly Ala Gly Thr
 1               5                  10                  15

Cys Cys Ala Ile Ser Leu Trp Leu Arg Gly Leu Arg Met Cys Thr Pro
                20                  25                  30

Leu Gly Arg Glu Gly Glu Glu Cys His Pro Gly Ser His Lys Val Pro
            35                  40                  45

Phe Phe Arg Lys Arg Lys His His Thr Cys Pro Cys Leu Pro Asn Leu
```

```
                        50                  55                  60
Leu Cys Ser Arg Phe Pro Asp Gly Arg Tyr Arg Cys Ser Met Asp Leu
 65                  70                  75                  80

Lys Asn Ile Asn Phe
                 85

<210> SEQ ID NO 17
<211> LENGTH: 86
<212> TYPE: PRT
<213> ORGANISM: Artificial Sequence
<220> FEATURE:
<223> OTHER INFORMATION: synthetic construct

<400> SEQUENCE: 17

Ala Ala Ala Ala Ala Ala Cys Glu Arg Asp Val Gln Cys Gly Ala Gly
 1               5                  10                  15

Thr Cys Cys Ala Ile Ser Leu Trp Leu Arg Gly Leu Arg Met Cys Thr
                 20                  25                  30

Pro Leu Gly Arg Glu Gly Glu Glu Cys His Pro Gly Ser His Lys Val
             35                  40                  45

Pro Phe Phe Arg Lys Arg Lys His His Thr Cys Pro Cys Leu Pro Asn
         50                  55                  60

Leu Leu Cys Ser Arg Phe Pro Asp Gly Arg Tyr Arg Cys Ser Met Asp
 65                  70                  75                  80

Leu Lys Asn Ile Asn Phe
                 85

<210> SEQ ID NO 18
<211> LENGTH: 87
<212> TYPE: PRT
<213> ORGANISM: Artificial Sequence
<220> FEATURE:
<223> OTHER INFORMATION: synthetic construct

<400> SEQUENCE: 18

Met Ala Val Ile Thr Gly Ala Cys Glu Arg Asp Val Gln Cys Gly Ala
 1               5                  10                  15

Gly Thr Cys Cys Ala Ile Ser Leu Trp Leu Arg Gly Leu Arg Met Cys
                 20                  25                  30

Thr Pro Leu Gly Arg Glu Gly Glu Glu Cys His Pro Gly Ser His Lys
             35                  40                  45

Val Pro Phe Phe Arg Lys Arg Lys His His Thr Cys Pro Cys Leu Pro
         50                  55                  60

Asn Leu Leu Cys Ser Arg Phe Pro Asp Gly Arg Tyr Arg Cys Ser Met
 65                  70                  75                  80

Asp Leu Lys Asn Ile Asn Phe
                 85

<210> SEQ ID NO 19
<211> LENGTH: 14
<212> TYPE: PRT
<213> ORGANISM: Artificial Sequence
<220> FEATURE:
<223> OTHER INFORMATION: synthetic construct

<400> SEQUENCE: 19

Ala Val Ile Thr Gly Ala Cys Glu Arg Asp Val Gln Cys Gly
 1               5                  10

<210> SEQ ID NO 20
```

-continued

<211> LENGTH: 86
<212> TYPE: PRT
<213> ORGANISM: Homo sapiens

<400> SEQUENCE: 20

Met Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Val
        35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys Asn Ile Asn Phe
                85

<210> SEQ ID NO 21
<211> LENGTH: 6
<212> TYPE: PRT
<213> ORGANISM: Homo sapiens

<400> SEQUENCE: 21

Ala Val Ile Thr Gly Ala
1               5

<210> SEQ ID NO 22
<211> LENGTH: 5
<212> TYPE: PRT
<213> ORGANISM: Homo sapiens

<400> SEQUENCE: 22

Val Ile Thr Gly Ala
1               5

<210> SEQ ID NO 23
<211> LENGTH: 7
<212> TYPE: PRT
<213> ORGANISM: Homo sapiens

<400> SEQUENCE: 23

Met Ala Val Ile Thr Gly Ala
1               5

<210> SEQ ID NO 24
<211> LENGTH: 393
<212> TYPE: PRT
<213> ORGANISM: Homo sapiens

<400> SEQUENCE: 24

Met Glu Thr Thr Met Gly Phe Met Asp Asp Asn Ala Thr Asn Thr Ser
1               5                   10                  15

Thr Ser Phe Leu Ser Val Leu Asn Pro His Gly Ala His Ala Thr Ser
            20                  25                  30

Phe Pro Phe Asn Phe Ser Tyr Ser Asp Tyr Asp Met Pro Leu Asp Glu
        35                  40                  45

Asp Glu Asp Val Thr Asn Ser Arg Thr Phe Phe Ala Ala Lys Ile Val
    50                  55                  60

Ile Gly Met Ala Leu Val Gly Ile Met Leu Val Cys Gly Ile Gly Asn
65                  70                  75                  80

```
Phe Ile Phe Ile Ala Ala Leu Val Arg Tyr Lys Lys Leu Arg Asn Leu
                85                  90                  95
Thr Asn Leu Leu Ile Ala Asn Leu Ala Ile Ser Asp Phe Leu Val Ala
            100                 105                 110
Ile Val Cys Cys Pro Phe Glu Met Asp Tyr Tyr Val Arg Gln Leu
        115                 120                 125
Ser Trp Glu His Gly His Val Leu Cys Thr Ser Val Asn Tyr Leu Arg
    130                 135                 140
Thr Val Ser Leu Tyr Val Ser Thr Asn Ala Leu Leu Ala Ile Ala Ile
145                 150                 155                 160
Asp Arg Tyr Leu Ala Ile Val His Pro Leu Arg Pro Arg Met Lys Cys
                165                 170                 175
Gln Thr Ala Thr Gly Leu Ile Ala Leu Val Trp Thr Val Ser Ile Leu
            180                 185                 190
Ile Ala Ile Pro Ser Ala Tyr Phe Thr Thr Glu Thr Val Leu Val Ile
        195                 200                 205
Val Lys Ser Gln Glu Lys Ile Phe Cys Gly Gln Ile Trp Pro Val Asp
    210                 215                 220
Gln Gln Leu Tyr Tyr Lys Ser Tyr Phe Leu Phe Ile Phe Gly Ile Glu
225                 230                 235                 240
Phe Val Gly Pro Val Val Thr Met Thr Leu Cys Tyr Ala Arg Met Thr
                245                 250                 255
Arg Glu Leu Trp Phe Lys Ala Val Pro Gly Phe Gln Thr Glu Gln Ile
            260                 265                 270
Arg Lys Arg Leu Arg Cys Arg Arg Lys Thr Val Leu Val Leu Met Cys
        275                 280                 285
Ile Leu Thr Ala Tyr Val Leu Cys Trp Ala Pro Phe Tyr Gly Phe Thr
    290                 295                 300
Ile Val Arg Asp Phe Phe Pro Thr Val Phe Val Lys Glu Lys His Tyr
305                 310                 315                 320
Leu Thr Ala Phe Tyr Ile Val Glu Cys Ile Ala Met Ser Asn Ser Met
                325                 330                 335
Ile Asn Thr Leu Cys Phe Val Thr Val Lys Asn Asp Thr Val Lys Tyr
            340                 345                 350
Phe Lys Lys Ile Met Leu Leu His Trp Lys Ala Ser Tyr Asn Gly Gly
        355                 360                 365
Lys Ser Ser Ala Asp Leu Asp Leu Lys Thr Ile Gly Met Pro Ala Thr
370                 375                 380
Glu Glu Val Asp Cys Ile Arg Leu Lys
385                 390

<210> SEQ ID NO 25
<211> LENGTH: 384
<212> TYPE: PRT
<213> ORGANISM: Homo sapiens

<400> SEQUENCE: 25

Met Ala Ala Gln Asn Gly Asn Thr Ser Phe Thr Pro Asn Phe Asn Pro
  1               5                  10                  15
Pro Gln Asp His Ala Ser Ser Leu Ser Phe Asn Phe Ser Tyr Gly Asp
                20                  25                  30
Tyr Asp Leu Pro Met Asp Glu Asp Glu Asp Met Thr Lys Thr Arg Thr
            35                  40                  45
Phe Phe Ala Ala Lys Ile Val Ile Gly Ile Ala Leu Ala Gly Ile Met
```

```
                50                  55                  60
Leu Val Cys Gly Ile Gly Asn Phe Val Phe Ile Ala Ala Leu Thr Arg
 65                  70                  75                  80

Tyr Lys Lys Leu Arg Asn Leu Thr Asn Leu Leu Ile Ala Asn Leu Ala
                 85                  90                  95

Ile Ser Asp Phe Leu Val Ala Ile Ile Cys Cys Pro Phe Glu Met Asp
                100                 105                 110

Tyr Tyr Val Val Arg Gln Leu Ser Trp Glu His Gly His Val Leu Cys
                115                 120                 125

Ala Ser Val Asn Tyr Leu Arg Thr Val Ser Leu Tyr Val Ser Thr Asn
130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                165                 170                 175

Val Trp Met Val Ser Ile Leu Ile Ala Ile Pro Ser Ala Tyr Phe Ala
                180                 185                 190

Thr Glu Thr Val Leu Phe Ile Val Lys Ser Gln Glu Lys Ile Phe Cys
                195                 200                 205

Gly Gln Ile Trp Pro Val Asp Gln Gln Leu Tyr Tyr Lys Ser Tyr Phe
                210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                245                 250                 255

Gly Phe Gln Thr Glu Gln Ile Arg Lys Arg Leu Arg Cys Arg Arg Lys
                260                 265                 270

Thr Val Leu Val Leu Met Cys Ile Leu Thr Ala Tyr Val Leu Cys Trp
                275                 280                 285

Ala Pro Phe Tyr Gly Phe Thr Ile Val Arg Asp Phe Phe Pro Thr Val
                290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                325                 330                 335

Lys Asn Asn Thr Met Lys Tyr Phe Lys Lys Met Met Leu Leu His Trp
                340                 345                 350

Arg Pro Ser Gln Arg Gly Ser Lys Ser Ser Ala Asp Leu Asp Leu Arg
                355                 360                 365

Thr Asn Gly Val Pro Thr Thr Glu Val Asp Cys Ile Arg Leu Lys
370                 375                 380

<210> SEQ ID NO 26
<211> LENGTH: 393
<212> TYPE: PRT
<213> ORGANISM: Mus musculus

<400> SEQUENCE: 26

Met Glu Thr Thr Val Gly Ala Leu Gly Glu Asn Thr Thr Asp Thr Phe
 1                   5                  10                  15

Thr Asp Phe Phe Ser Ala Leu Asp Gly His Glu Ala Gln Thr Gly Ser
                 20                  25                  30

Leu Pro Phe Thr Phe Ser Tyr Gly Asp Tyr Asp Met Pro Leu Asp Glu
                 35                  40                  45
```

-continued

```
Glu Glu Asp Val Thr Asn Ser Arg Thr Phe Phe Ala Ala Lys Ile Val
 50                  55                  60

Ile Gly Met Ala Leu Val Gly Ile Met Leu Val Cys Gly Ile Gly Asn
 65                  70                  75                  80

Phe Ile Phe Ile Thr Ala Leu Ala Arg Tyr Lys Lys Leu Arg Asn Leu
                 85                  90                  95

Thr Asn Leu Leu Ile Ala Asn Leu Ala Ile Ser Asp Phe Leu Val Ala
            100                 105                 110

Ile Val Cys Cys Pro Phe Glu Met Asp Tyr Tyr Val Arg Gln Leu
        115                 120                 125

Ser Trp Glu His Gly His Val Leu Cys Ala Ser Val Asn Tyr Leu Arg
130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                165                 170                 175

Gln Thr Ala Ala Gly Leu Ile Phe Leu Val Trp Ser Val Ser Ile Leu
            180                 185                 190

Ile Ala Ile Pro Ala Ala Tyr Phe Thr Thr Glu Thr Val Leu Val Ile
        195                 200                 205

Val Glu Arg Gln Glu Lys Ile Phe Cys Gly Gln Ile Trp Pro Val Asp
210                 215                 220

Gln Gln Phe Tyr Tyr Arg Ser Tyr Phe Leu Leu Val Phe Gly Leu Glu
225                 230                 235                 240

Phe Val Gly Pro Val Val Ala Met Thr Leu Cys Tyr Ala Arg Val Ser
                245                 250                 255

Arg Glu Leu Trp Phe Lys Ala Val Pro Gly Phe Gln Thr Glu Gln Ile
            260                 265                 270

Arg Arg Thr Val Arg Cys Arg Arg Thr Val Leu Gly Leu Val Cys
        275                 280                 285

Val Leu Ser Ala Tyr Val Leu Cys Trp Ala Pro Phe Tyr Gly Phe Thr
290                 295                 300

Ile Val Arg Asp Phe Phe Pro Ser Val Phe Lys Glu Lys His Tyr
305                 310                 315                 320

Leu Thr Ala Phe Tyr Val Val Glu Cys Ile Ala Met Ser Asn Ser Met
                325                 330                 335

Ile Asn Thr Leu Cys Phe Val Thr Val Arg Asn Asn Thr Ser Lys Tyr
            340                 345                 350

Leu Lys Arg Ile Leu Arg Leu Gln Trp Arg Ala Ser Pro Ser Gly Ser
        355                 360                 365

Lys Ala Ser Ala Asp Leu Asp Leu Arg Thr Thr Gly Ile Pro Ala Thr
370                 375                 380

Glu Glu Val Asp Cys Ile Arg Leu Lys
385                 390
```

<210> SEQ ID NO 27
<211> LENGTH: 381
<212> TYPE: PRT
<213> ORGANISM: Mus musculus

<400> SEQUENCE: 27

```
Met Gly Pro Gln Asn Arg Asn Thr Ser Phe Ala Pro Asp Leu Asn Pro
  1               5                  10                  15

Pro Gln Asp His Val Ser Leu Asn Tyr Ser Tyr Gly Asp Tyr Asp Leu
             20                  25                  30
```

```
Pro Leu Gly Glu Asp Glu Asp Val Thr Lys Thr Gln Thr Phe Phe Ala
        35                  40                  45

Ala Lys Ile Val Ile Gly Val Ala Leu Ala Gly Ile Met Leu Val Cys
 50                  55                  60

Gly Ile Gly Asn Phe Val Phe Ile Ala Ala Leu Ala Arg Tyr Lys Lys
 65                  70                  75                  80

Leu Arg Asn Leu Thr Asn Leu Leu Ile Ala Asn Leu Ala Ile Ser Asp
                 85                  90                  95

Phe Leu Val Ala Ile Val Cys Cys Pro Phe Glu Met Asp Tyr Tyr Val
            100                 105                 110

Val Arg Gln Leu Ser Trp Ala His Gly His Val Leu Cys Ala Ser Val
        115                 120                 125

Asn Tyr Leu Arg Thr Val Ser Leu Tyr Val Ser Thr Asn Ala Leu Leu
    130                 135                 140

Ala Ile Ala Ile Asp Arg Tyr Leu Ala Ile Val His Pro Leu Lys Pro
145                 150                 155                 160

Arg Met Asn Tyr Gln Thr Ala Ser Phe Leu Ile Ala Leu Val Trp Met
                165                 170                 175

Val Ser Ile Leu Ile Ala Val Pro Ser Ala Tyr Phe Thr Thr Glu Thr
            180                 185                 190

Ile Leu Val Ile Val Lys Asn Gln Glu Lys Ile Phe Cys Gly Gln Ile
        195                 200                 205

Trp Ser Val Asp Gln Gln Leu Tyr Tyr Lys Ser Tyr Phe Leu Phe Val
    210                 215                 220

Phe Gly Leu Glu Phe Val Gly Pro Val Val Thr Met Thr Leu Cys Tyr
225                 230                 235                 240

Ala Arg Ile Ser Gln Glu Leu Trp Phe Lys Ala Val Pro Gly Phe Gln
                245                 250                 255

Thr Glu Gln Ile Arg Lys Arg Leu Arg Cys Arg Arg Lys Thr Val Leu
            260                 265                 270

Leu Leu Met Gly Ile Leu Thr Ala Tyr Val Leu Cys Trp Ala Pro Phe
        275                 280                 285

Tyr Gly Phe Thr Ile Val Arg Asp Phe Phe Pro Thr Val Val Val Lys
    290                 295                 300

Glu Lys His Tyr Leu Thr Ala Phe Tyr Val Val Glu Cys Ile Ala Met
305                 310                 315                 320

Ser Asn Ser Met Ile Asn Thr Ile Cys Phe Val Thr Val Lys Asn Asn
                325                 330                 335

Thr Met Lys Tyr Phe Lys Lys Met Leu Arg Leu His Trp Arg Pro Ser
            340                 345                 350

His Tyr Gly Ser Lys Ser Ser Ala Asp Leu Asp Leu Lys Thr Ser Gly
        355                 360                 365

Val Pro Ala Thr Glu Val Asp Cys Ile Arg Leu Lys
    370                 375                 380

<210> SEQ ID NO 28
<211> LENGTH: 86
<212> TYPE: PRT
<213> ORGANISM: Mus musculus

<400> SEQUENCE: 28

Ala Val Ile Thr Gly Ala Cys Glu Arg Asp Ile Gln Cys Gly Ala Gly
 1               5                  10                  15

Thr Cys Cys Ala Ile Ser Leu Trp Leu Arg Gly Leu Arg Leu Cys Thr
```

```
                     20                  25                  30
Pro Leu Gly Arg Glu Gly Glu Cys His Pro Gly Ser His Lys Ile
             35                  40                  45

Pro Phe Leu Arg Lys Arg Gln His His Thr Cys Pro Cys Ser Pro Ser
 50                  55                  60

Leu Leu Cys Ser Arg Phe Pro Asp Gly Arg Tyr Arg Cys Phe Arg Asp
 65                  70                  75                  80

Leu Lys Asn Ala Asn Phe
                 85

<210> SEQ ID NO 29
<211> LENGTH: 81
<212> TYPE: PRT
<213> ORGANISM: Mus musculus

<400> SEQUENCE: 29

Ala Val Ile Thr Gly Ala Cys Asp Lys Asp Ser Gln Cys Gly Gly Gly
 1               5                  10                  15

Met Cys Cys Ala Val Ser Ile Trp Val Lys Ser Ile Arg Ile Cys Thr
                 20                  25                  30

Pro Met Gly Gln Val Gly Asp Ser Cys His Pro Leu Thr Arg Lys Val
             35                  40                  45

Pro Phe Trp Gly Arg Arg Met His His Thr Cys Pro Cys Leu Pro Gly
 50                  55                  60

Leu Ala Cys Leu Arg Thr Ser Phe Asn Arg Phe Ile Cys Leu Ala Arg
 65                  70                  75                  80

Lys

<210> SEQ ID NO 30
<211> LENGTH: 86
<212> TYPE: PRT
<213> ORGANISM: Rattus sp.

<400> SEQUENCE: 30

Ala Val Ile Thr Gly Ala Cys Glu Arg Asp Val Gln Cys Gly Ala Gly
 1               5                  10                  15

Thr Cys Cys Ala Ile Ser Leu Trp Leu Arg Gly Leu Arg Leu Cys Thr
                 20                  25                  30

Pro Leu Gly Arg Glu Gly Glu Cys His Pro Gly Ser His Lys Ile
             35                  40                  45

Pro Phe Phe Arg Lys Arg Gln His His Thr Cys Pro Cys Ser Pro Ser
 50                  55                  60

Leu Leu Cys Ser Arg Phe Pro Asp Gly Arg Tyr Arg Cys Ser Gln Asp
 65                  70                  75                  80

Leu Lys Asn Val Asn Phe
                 85

<210> SEQ ID NO 31
<211> LENGTH: 81
<212> TYPE: PRT
<213> ORGANISM: Rattus sp.

<400> SEQUENCE: 31

Ala Val Ile Thr Gly Ala Cys Asp Lys Asp Ser Gln Cys Gly Gly Gly
 1               5                  10                  15

Met Cys Cys Ala Val Ser Ile Trp Val Lys Ser Ile Arg Ile Cys Thr
                 20                  25                  30
```

```
-continued

Pro Met Gly Gln Val Gly Asp Ser Cys His Pro Leu Thr Arg Lys Val
        35                  40                  45

Pro Phe Trp Gly Arg Arg Met His His Thr Cys Pro Cys Leu Pro Gly
    50                  55                  60

Leu Ala Cys Leu Arg Thr Ser Phe Asn Arg Phe Ile Cys Leu Ala Arg
65                  70                  75                  80

Lys

<210> SEQ ID NO 32
<211> LENGTH: 77
<212> TYPE: PRT
<213> ORGANISM: Bombina maxima

<400> SEQUENCE: 32

Ala Val Ile Thr Gly Ala Cys Asp Arg Asp Val Gln Cys Gly Ser Gly
1               5                   10                  15

Thr Cys Cys Ala Ala Ser Leu Trp Ser Arg Asn Ile Arg Phe Cys Val
                20                  25                  30

Pro Leu Gly Asn Asn Gly Glu Glu Cys His Pro Ala Ser His Lys Val
            35                  40                  45

Pro Tyr Asn Gly Lys Arg Leu Ser Ser Leu Cys Pro Cys Lys Ser Gly
    50                  55                  60

Leu Thr Cys Ser Lys Ser Gly Glu Lys Phe Gln Cys Ser
65                  70                  75
```

METHODS FOR MODULATING GASTRIC SECRETION USING PROKINETICIN RECEPTOR ANTAGONISTS

This application claims the benefit of U.S. Provisional Application No. 60/457,891, filed Mar. 25, 2003, which is incorporated hereby by reference.

BACKGROUND OF THE INVENTION

This invention relates generally to gastrological diseases and, more specifically, to modulating gastric acid and pepsinogen secretion to reduce or treat such diseases.

Gastrointestinal problems are common. Most people have experienced some form of gastrointestinal upset in their lives: nausea, vomiting or diarrhea associated with the flu, or indigestion after eating excessively. Over 95 million Americans have experienced gastrointestinal upset, and over 10 million Americans are hospitalized each year for care of gastrointestinal problems. While many digestive problems are more common as people get older, they can occur at any age, even in children, and strike regardless of gender, ethnic or socioeconomic backgrounds. Heartburn and ulcers are well known examples of common gastrointestinal problems. These disorders result from and are exacerbated by excessive secretion of gastric acid in the digestive tract.

Heartburn, also known as acid indigestion or Gastroesophageal Reflux Disease (GERD), is caused by the backward flow of acid from the stomach up into the esophagus. People with heartburn experience burning chest pain localized behind the breastbone that moves up toward the neck and throat. Some even experience a bitter or sour taste of acid in the back of the throat. The burning and pressure symptoms of heartburn can last as long as 2 hours and are often worsened by eating food. At least 60 million Americans experience heartburn at least once a month and some studies have suggested that over 15 million Americans experience heartburn daily.

Peptic ulcers are crater-like lesions of the gastrointestinal tract that can be caused by an inflammatory, infectious, or malignant condition. People with ulcers can experience a gnawing, burning pain in the upper abdomen; nausea; vomiting; loss of appetite; and weight loss. About 20 million Americans will suffer from an ulcer in their lifetime. Duodenal ulcers often occur between the ages of 30 and 50, and are twice as common among men. Stomach ulcers are more common after the age of 60 and are more commonly seen in women.

Medications for treating gastrointestinal disorders relating to excessive acid secretion are currently available. However, these medications fail to alleviate symptoms in a significant number of patients, up to 50% of patients for certain classes of medications. Such patients continue to experience gastrointestinal discomfort that many would agree has reduced their quality of life.

Thus, there exists a need for methods for modulating gastric acid and pepsinogen secretion. The present invention satisfies this need and provides related advantages as well.

SUMMARY OF THE INVENTION

The invention provides methods of modulating gastric acid or pepsinogen secretion by administering an amount of a prokineticin receptor antagonist effective to alter one or more indicia of gastric acid secretion, wherein the antagonist contains an amino acid sequence at least 80% identical to amino acids to 7 to 77 of SEQ ID NO:3, which includes (a) the 10 conserved cysteine residues of SEQ ID NO:3, and (b) from 0 to 9 of amino acids 78 to 86 of SEQ ID NO:3, wherein amino acids 1 to 6 of the antagonist do not consist of amino acids AVITGA (SEQ ID NO:21).

In another embodiment, the method involves administering an amount of a prokineticin receptor antagonist effective to alter one or more indicia of gastric acid or pepsinogen secretion, wherein the antagonist contains an amino acid sequence at least 80% identical to amino acids to 7 to 77 of SEQ ID NO:6, which includes (a) the 10 conserved cysteine residues of SEQ ID NO:6, and (b) from 0 to 4 of amino acids 78 to 81 of SEQ ID NO:6, wherein amino acids 1 to 6 of the antagonist do not consist of amino acids AVITGA (SEQ ID NO:21).

A PK receptor antagonist used in a method of the invention can contain a substitution, deletion or addition with respect to wild-type amino acids 1 to 6 of prokineticins, such as those referenced as SEQ ID NOS:3 and 6. A PK receptor antagonist can contain, for example, 6 or more amino acids N-terminal to the conserved cysteine residue, which can be, for example, MAVITGA (SEQ ID NO:23). A PK receptor antagonist also can contain 5 or fewer amino acids N-terminal to the first conserved cysteine residue, which can be, for example, VITGA (SEQ ID NO:22).

A PK receptor antagonist used in a method of the invention can contain amino acid residues that differ from residues 7 to 77 of SEQ ID NO:3 or SEQ ID NO:6, which can be, for example, conservative substitutions of these residues. In addition, amino acid residues that differ from residues 7 to 77 of SEQ ID NO:3 can be the corresponding residues from SEQ ID NO:6. Likewise, amino acid residues that differ from residues 7 to 77 of SEQ ID NO:6 can be the corresponding residues from SEQ ID NO:3.

A method of the invention for modulating gastric acid or pepsinogen secretion can involve administering a PK receptor antagonist to cell, tissue or animal, capable of exhibiting an index of gastric acid or pepsinogen secretion, and can be used to beneficially treat disorders and diseases characterized by acid-related gastrointestinal damage.

The invention further provides method for screening for a compound for modulating gastric acid or pepsinogen secretion in a mammal. The method involves (a) providing a compound that is a prokineticin (PK) receptor antagonist or agonist; and (b) determining the ability of the compound to modulate one or more indicia of gastric acid or pepsinogen secretion, wherein a compound that modulates the one or more indicia is identified as a compound for modulating gastric acid or pepsinogen secretion in a mammal.

DETAILED DESCRIPTION OF THE INVENTION

Figure 1A:
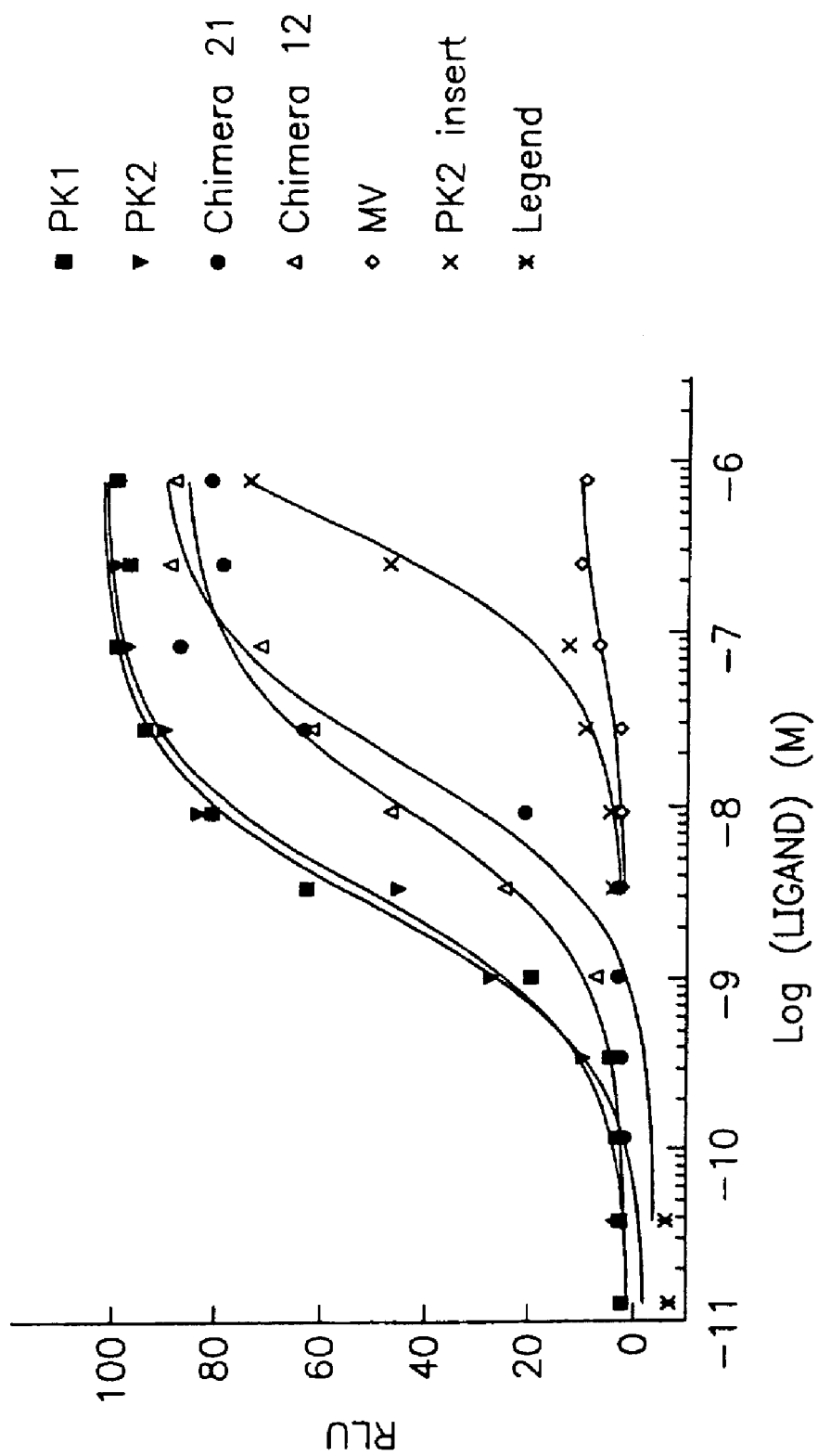
FIG. 1A shows a dose-response curve of several prokineticins and prokineticin receptor (PKR) antagonists assayed for their ability to modulate prokineticin receptor 1 (PKR1)-mediated calcium mobilization.
Figure 1B:
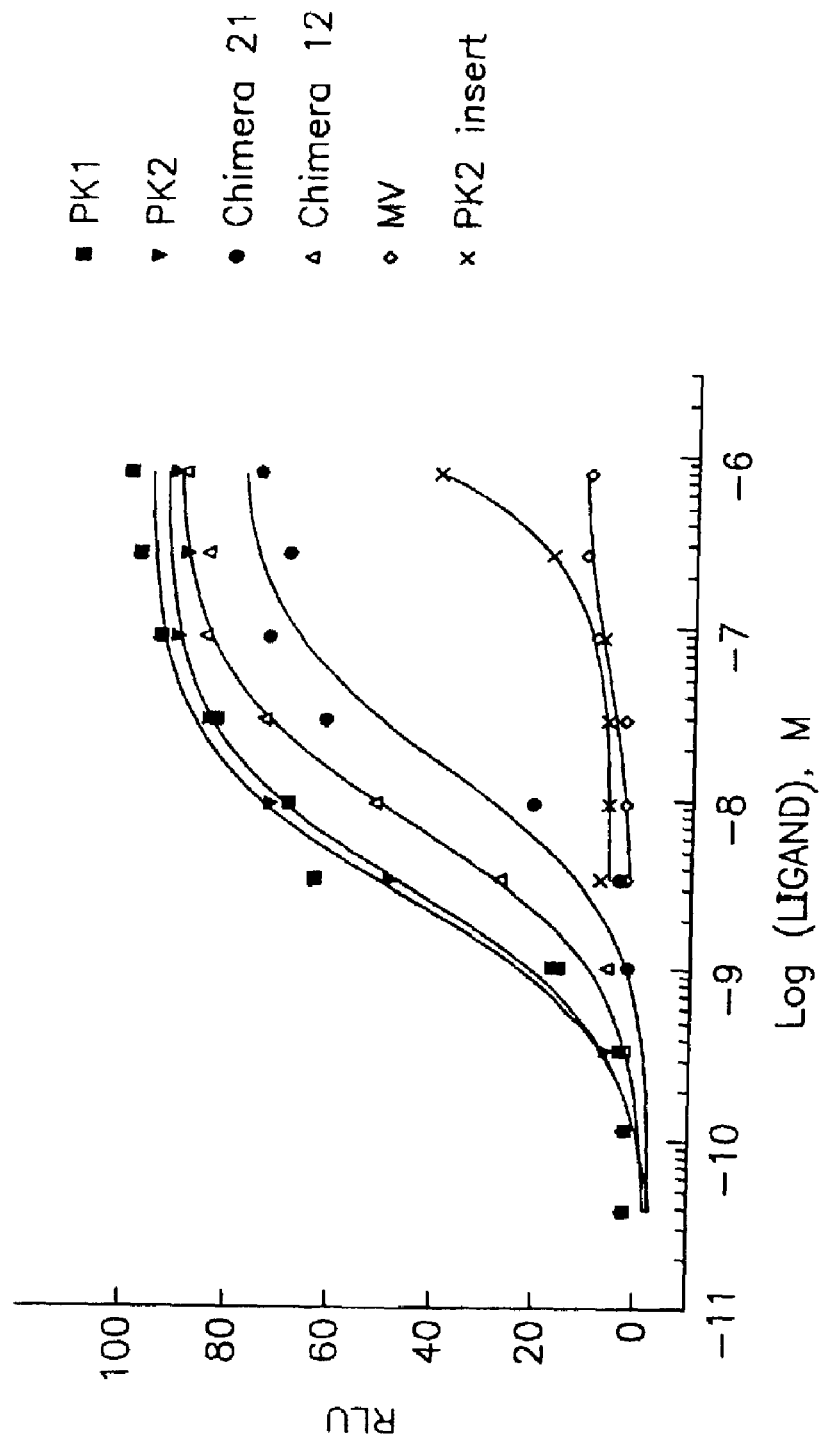
FIG. 1B shows a dose-response curve of various prokineticins (PKs) and prokineticin receptor antagonists assayed for their ability to modulate prokineticin receptor 2 (PKR2)-mediated calcium mobilization.

The present invention relates to the determination that prokineticin receptors and prokineticins are expressed in the stomach, and that prokineticin receptor antagonists can be used to modulate gastric acid or pepsinogen secretion mediated a prokineticin receptor (PKR). As described herein, PK receptor antagonists that are N-terminally modified forms of PKS have the ability to modulate signaling mediated by prokineticin receptors. Such PK receptor antagonists can reduce or inhibit gastric acid or pepsinogen secretion in PK receptor expressing tissues.

Unwanted or excessive secretion of gastric acid into the gastrointestinal tract can damage tissues and lead to a number of conditions that cause significant discomfort to individuals. Normally, to prevent gastric acid from digesting gastrointestinal tract tissue, the body uses a number of protective mechanisms, including bicarbonate secretion to neutralize acid, mucous secretion to form a protective barrier, rapid turnover of epithelial cells that line the tract, enhanced blood supply to digestive organs, and use of sphincters to contain acid in the stomach.

If this protection is compromised, gastric acid attacks the lining of the gastrointestinal tract. This can result in discomfort, heartburn, ulcer formation, and severe stomach pain. If left untreated, ulcers can damage underlying blood vessels, and may perforate the stomach wall.

A PK receptor antagonist can be used to beneficially modulate gastric acid or pepsinogen secretion in an individual. Methods for modulating gastric acid secretion have a variety of applications, including treating individuals having, or who are likely to develop, disorders characterized by acid-related gastrointestinal damage, as described in more detail below. Therapeutic methods of modulating gastric acid secretion involve administering a PK receptor antagonist to an animal, for example to treat gastric lesions, such as gastric ulcer and duodenal ulcer.

A PK receptor antagonist can be used in methods for prevention and treatment of a variety of gastric-acid related diseases in mammals, including humans. Non-limiting examples of such diseases include reflux esophagitis, gastritis, and duodenitis. Furthermore, a PK receptor antagonist can be used in methods for treatment of other conditions or gastrointestinal disorders where gastric acid inhibitory effect is desirable, for example, in patients having NSAID therapy, patients having Non Ulcer Dyspepsia, in patients having symptomatic gastro-esophageal reflux disease (GERD), in patients having gastrinomas, gastric carcinoma and other proliferative stomach diseases, and in patients having lower gastrointestinal disorders, such as irritable bowel syndrome, functional diarrhea, microscopic colitis, lymphocytic colitis, infectious diarrhea, lactase deficiency, infectious diarrhea, amebiasis, giardiasis, a viral infection, cytomegalovirus infection, a pathogenic bacterial infection, an infection by a bacterium of the genus *Escherichia*, an *Escherichia coli* 0157:H7 infection, an infection by a bacterium of the genus *Salmonella*, an infection by a bacterium of the genus *Shigella*, an infection by a bacterium of the genus *Campylobacter*, or an infection by a bacterium of the genus *Yersinia*. A PK receptor antagonist also be used in methods for treating patients in intensive care situations, in patients with acute upper gastrointestinal bleeding, pre-and postoperatively to prevent aspiration of gastric acid and to prevent and treat stress ulceration. Further, a PK receptor antagonist can be used in methods for treating *Helicobacter pylori* infections and related diseases.

Accordingly, the invention provides methods of modulating gastric acid secretion by administering a PK receptor antagonist, which has a structure described herein below, in an amount effective to alter one or more indicia of gastric acid secretion.

The methods of the invention involve modulating gastric acid or pepsinogen secretion by administering a PK receptor antagonist described herein below. As used herein, the term "prokineticin receptor antagonist," or "PKR antagonist" refers to a compound that inhibits or decreases normal G-protein coupled signal transduction through a PK receptor. A PK receptor antagonist can act by any antagonistic mechanism, such as by directly binding a PK receptor at the PK binding site, thereby inhibiting binding between the PK receptor and its ligand. A PK receptor antagonist can also act indirectly, for example, by binding a PK. The term "PK receptor antagonist" is also intended to include compounds that act as "inverse agonists," meaning that they decrease PK receptor signaling from a baseline amount of constitutive signaling activity. A PK receptor antagonist can optionally be selective for PKR1 or PKR2, or alternatively be equally active with respect to both PKR1 and PKR2.

Those skilled in the art will recognize that a PK receptor agonist can be useful for promoting or increasing gastric acid or pepsinogen secretion. As non-limiting examples, PK receptor agonist can be used to increase levels of gastric acid secretion in patients for treatment of indigestion, and in patients having gastric mucosa that has undergone hypertrophy, for example, in response to massive enterectomy or to creation of a permanent enterostomy. A PK receptor agonist is a compound that selectively promotes or enhances normal signal transduction through the PK receptor. A PK receptor agonist can act by any agonistic mechanism, such as by binding a PK receptor at the normal PK binding site, thereby promoting PK receptor signaling. A PK receptor agonist can also act, for example, by potentiating the binding activity of PK or signaling activity of PK receptor. A PK receptor agonist can also be an inverse agonist, which decreases PK receptor signaling from a baseline amount of constitutive PK receptor signaling activity. A PK receptor agonist can optionally be selective for PKR1 or PKR2, or alternatively be equally active with respect to both PKR1 and PKR2. Exemplary PK receptor agonists include prokineticins from a variety of species including those described herein, and chimeric prokinetins including those described herein.

In a method of the invention for modulating gastric acid or pepsinogen secretion, a PK receptor antagonist or agonist can be administered to a cell that contains a PK receptor, or a tissue or animal containing such a cell, that is capable of exhibiting an index of gastric acid or pepsinogen secretion. As used herein, the term "prokineticin receptor," "PK receptor," or "PKR" refers to a heptahelical membrane-spanning polypeptide that binds to a prokineticin and signals through a G-protein coupled signal transduction pathway in response to prokineticin binding. Prokineticin receptors are believed to couple to the Gα subtype known as Gαq, and thereby mediate intracellular calcium mobilization through a MAPK activation-dependent signaling pathway in response to agonists. A detailed description of prokineticin receptors that can be modulated by a PK receptor antagonist or agonist is provided herein below.

A PK receptor antagonist useful in a method of the invention for modulating angiogenesis can be a modified prokineticin (PK). As used herein, the term "prokineticin" or "PK" refers to a peptide that binds to a prokineticin receptor and elicits signaling by the receptor through a G-protein coupled signal transduction pathway.

A PK receptor antagonist can be a modified version of a naturally-occurring amino acid sequence of a PK from any species. Such a PK can be, for example, a modified mammalian PK, such as human PK1 (SEQ ID NO:3; GenBank Accession No. P58294; also known as endocrine-gland-derived endothelial growth factor or EG-VEGF, TANGO 266, PRO 1186 and Zven2; Li et al., supra (2001), LeCouter et al., Nature 412: 877–884 (2001), WO 01/36465, WO 99/63088 and WO 00/52022; a modified human PK2 (GenBank Accession No. Q9HC23; isoform 1, SEQ ID NO:6, Wechselberger et al., FEBS Lett. 462:177–181 (1999) or isoform 2, SEQ ID NO:5; also known as Zven1, Li et al., supra (2001)); a modified mouse PK1 (SEQ ID NO:28; GenBank Accession No. AAM49573); a modified mouse PK2 (SEQ ID NO:29; GenBank Accession No. AAM49572); a modified rat PK1 (SEQ ID NO:30; GenBank Accession No. AAM09104; Masuda et al., supra (2002)); a modified rat PK2 (SEQ ID NO:31; GenBank Accession No. AAM09105; Masuda et al., supra (2002)), or a modified PK from another mammalian species, such as a modified primate, dog, cat, pig, cow, sheep or goat PK.

A PK receptor antagonist can alternatively be a modified version of a PK of another vertebrate species, such as a snake, frog or toad. For example, the modified PK can be a modified black mamba PK (SEQ ID NO:12; GenBank Accession No. P25687; also known as MIT1; Schweitz et al., FEBS Lett. 461:183–188 (1999)); a modified Bombina variegata frog PK (SEQ ID NO:11; GenBank Accession No. Q9PW66; also known as Bv8; Mollay et al., Eur. J. Pharmacol. 374:189–196 (1999); a modified Bombina maxima toad PK (SEQ ID NO:32; GenBank Accession No. AAN03822), or a modified PK from another vertebrate species, such as a modified amphibian, reptile, fish or bird PK.

A PK receptor antagonist also can be a modification of a chimeric PK, such as a modification of a human prokineticin chimera having SEQ ID NO:13 (chimera of PK1 at N-terminus, PK2 at C-terminus) or SEQ ID NO:14 (chimera of PK2 at N-terminus, PK1 at C-terminus).

Exemplary PK receptor antagonists useful in a method of the invention include modified prokineticin polypeptides containing the 10 conserved cysteine residues of wild type prokineticins and the conserved C-terminal residues of wild type prokineticins, but having N-terminal regions different from those of wild-type prokineticins. An N-terminal region of a PK receptor antagonist can include, for example, an addition, deletion or substitution with respect to the six N-terminal amino acids of prokineticins (AVITGA), or an addition or deletion in combination with a substitution, so long as the modified prokineticin exhibits PK receptor antagonistic activity.

A PK receptor antagonist further can be a PK having an N-terminal covalent modification. A number of different reactions can be used to covalently modify a PK, for example, by attaching a moiety to one or more N-terminal amino acid residues. For example, a chemical group on an amino acid, such as an amine group of lysine, a free carboxylic acid group of glutamic or aspartic acid, a sulfhydryl group of cysteine or a moiety of an aromatic amino acids, can be modified using a variety of reagents well known to those skilled in the art. One or more selected chemical groups can be modified, for example, by covalent attachment of a moiety. Such moieties include, for example, an organic molecule, such as a dye, linker and detectable moiety, such as a fluorophore or luminescent compound; a macromolecule, such as a polypeptide, nucleic acid, carbohydrate, and lipid, or a modification thereof.

Chemical and enzymatic modifications to a PK to produce a PK receptor antagonist include, but are not limited to the following: replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation.

A PK receptor antagonist also can be a non-covalent modification of the N-terminus of a PK. A number of non-covalent interactions can be used to modify a PK. For example, the N-terminus of a PK can be modified by binding to an antibody or other antigen-binding molecule, including a polyclonal and monoclonal antibody, and antigen binding fragments of such antibodies, as well as a single chain antibody, chimeric antibody, bifunctional antibody, CDR-grafted antibody and humanized antibody, and antigen-binding fragments of such antibodies, or any other moiety that can be attached non-covalently to the N-terminus.

In one embodiment, a modified prokineticin that is a PK receptor antagonist is an N-terminal substitution mutant. Such a mutant can contain any amino acid residues at the six N-terminal amino acids of prokineticins except for AVITGA (SEQ ID NO:21); any amino acid residues at five or fewer amino acids N-terminal to the first conserved cysteine residue; or any amino acid residues at seven or more amino acids N-terminal to the first conserved cysteine residue so long as the mutant has PK receptor antagonistic activity. The N-terminal prokineticin mutant designated MV PK1 (SEQ ID NO:20) is an exemplary substitution mutant containing five amino acids N-terminal to the first conserved cysteine residue that has antagonistic activity.

In another embodiment, a modified prokineticin that is a PK receptor antagonist is an N-terminal addition mutant. Such a mutant can contain 6 or more amino acids N-terminal to the first conserved cysteine residue, such as 7 or more amino acids N-terminal to the first conserved cysteine residue, and 10 or more amino acids N-terminal to the first conserved cysteine residue. The 6 or more amino acids N-terminal to the first conserved cysteine can have any amino acid sequence so long as the mutant has PK receptor antagonistic activity. In one embodiment, a PK receptor antagonist useful in a method of the invention contains the sequence MAVITGA (SEQ ID NO:23) N-terminal to the first conserved cysteine residue. The N-terminal prokineticin mutant designated Met PK1 (SEQ ID NO:18) contains the sequence MAVITGA-terminal to the first conserved cysteine residue, and is an exemplary addition mutant having antagonistic activity.

Additions to a PK amino acid sequence to produce a PK receptor antagonist include, but are not limited to, the addition of "tag" sequences to the N-terminus. Such tag sequence include, for example, epitope tags, histidine tags, glutathione-S-transferase (GST), and the like, or sorting sequences.

A modified prokineticin that is a PK receptor antagonist can contain a substitution with respect to a defined prokineticin sequence. Substitutions to PK amino acid sequences, such as SEQ ID NOS:3 or 6, can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

In a further embodiment, a modified prokineticin that is a PK receptor antagonist is a N-terminal deletion mutant. Such a mutant can contain 5 or fewer amino acids N-terminal to the first conserved cysteine residue, such as 4 or fewer amino acids N-terminal to the first conserved cysteine residue, and 2 or fewer amino acids N-terminal to the first conserved cysteine residue, including 1 amino acid or no amino acids N-terminal to the first conserved cysteine residue. The 5 or fewer amino acids N-terminal to the first conserved cysteine can have any amino acid sequence so long as the mutant has PK receptor antagonistic activity. In one embodiment, a PK receptor antagonist useful in a method of the invention contains the sequence VITGA (SEQ ID NO:22) N-terminal to the first conserved cysteine residue. The N-terminal prokineticin mutant designated DelA PK1 (SEQ ID NO:16) contains the sequence VITGA-terminal to the first conserved cysteine and is an exemplary deletion mutant having antagonistic activity.

In one embodiment, a PK receptor antagonist useful in a method of the invention contains an amino acid sequence at least 80% identical to amino acids to 7 to 77 of SEQ ID NO:3, and includes (a) the 10 conserved cysteine residues of SEQ ID NO:3, and (b) from 0 to 9 of amino acids 78 to 86 of SEQ ID NO:3, wherein amino acids 1 to 6 of the antagonist do not consist of amino acids AVITGA (SEQ ID NO:21).

In another embodiment, a PK receptor antagonist useful in a method of the invention contains an amino acid sequence at least 80% identical to amino acids to 7 to 77 of SEQ ID NO:6, and includes (a) the 10 conserved cysteine residues of SEQ ID NO:6, and (b) from 0 to 4 of amino acids 78 to 81 of SEQ ID NO:6, wherein amino acids 1 to 6 of the antagonist do not consist of amino acids AVITGA (SEQ ID NO:21).

The amino acid residues that differ from residues 7 to 77 of SEQ ID NO:3 can be, for example, the corresponding residues from SEQ ID NO:6. Likewise, the amino acid residues that differ from residues 7 to 77 of SEQ ID NO:6 can be, for example, the corresponding residues from SEQ ID NO:3. In an embodiment, a PK receptor antagonist useful in a method of the invention contains amino acids 7 to 77 of SEQ ID NO:3. In another embodiment, a PK receptor antagonist useful in a method of the invention contains amino acids 7 to 77 of SEQ ID NO:6.

A prokineticin receptor antagonist therefore can be an amino acid sequence at least 80% identical to amino acids to 7 to 77 of SEQ ID NO:3 or 6, at least 90% identical to amino acids to 7 to 77 of SEQ ID NO:3, at least 95% identical to amino acids to 7 to 77 of SEQ ID NO:3 or 6, and at least 98% identical to amino acids to 7 to 77 of SEQ ID NO:3 or 6, including an amino acid sequence that is identical to amino acids 7 to 77 of SEQ ID NO:3 or 6.

A PK receptor antagonist useful in a method of the invention will generally have an $IC_{50}$ that is no more than 2-fold, 5-fold, 10-fold, 50-fold, 100-fold or 1000-fold higher or lower than the $EC_{50}$ for human PK1 or PK2 in the particular assay. For therapeutic applications described below, a PK receptor antagonist preferably has an $IC_{50}$, of less than about $10^{-7}$ M, such as less than $10^{-8}$ M, and more preferably less than $10^{-9}$ or $10_{-10}$ M. However, depending on the stability, selectivity and toxicity of the compound, a PK receptor antagonist with a higher $IC_{50}$, can also be useful therapeutically. As described in Example I and in Table 1, below, PK receptor antagonists Met PK1 and MV PK1 have nanomolar antagonist activity with respect to both PKR1 and PKR2, in the presence of either PK1 or PK2.

TABLE 1

Antagonistic Activity of PK mutants (Calcium Mobilization Assay)

| Receptor | Ligand | Met PK1 (nM) | MV PK1 (nM) |
| --- | --- | --- | --- |
| PKR1 | PK1 | 9 | 6 |
| PKR2 | PK2 | 30 | 29 |
| PKR2 | PK1 | 15 | 16 |
| PKR1 | PK2 | 90 | 110 |

A PK receptor modulated by a PK receptor antagonist in a method of the invention can be contained in a cell that is isolated or present in a tissue or animal.

In one embodiment, such a PK receptor can be contained within a naturally occurring cell or a cell that expresses recombinant PK receptor. A PK receptor that can be modulated by a PK receptor antagonist described herein above can have the naturally-occurring amino acid sequence of a PK receptor from any species, or can contain minor modifications with respect to the naturally-occurring sequence. For example, such a PK receptor can be a mammalian PK receptor, such as human PKR1 (SEQ ID NO:24; GenBank Accession No. AAM48127; also called GPR73, fb41a, hZAQ, hGPRv21 and EG-VEGF receptor-1; Lin et al., *J. Biol. Chem.* 277:19276–19280 (2002), Masuda et al., *Biochem. Biophys. Res. Commun.* 293:396–402 (2002), WO 00/34334, WO 01/48188 and WO 01/16309); human PKR2 (SEQ ID NO:25; GenBank Accession No. AAM48128; also known as I5E, hRUP8 and hZAQ2; Lin et al., supra (2002), Masuda et al., supra (2002), WO 98/46620, Wo 01/36471 and WO 02/06483); mouse PKR1 (SEQ ID NO:26; GenBank Accession No. AAM49570; Cheng et al., *Nature* 417:405–410 (2002) and WO 02/06483); mouse PKR2 (SEQ ID NO:27; GenBank Accession No. AAM49571; Cheng et al., supra (2002) and WO 02/06483); rat PKR1 (WO 02/06483); rat PKR2 (WO 02/06483); monkey PKR2 (also known as AXOR8; WO 01/53308); bovine PKR1

(Masuda et al., supra (2002), or a PKR of another mammalian species, such as other primate, dog, cat, pig, sheep or goat; or a PKR of another vertebrate species, such as an amphibian, reptile, fish or bird.

In a method of the invention, a PK receptor modulated by a PK receptor antagonist can contain minor modifications with respect to a naturally-occurring PK receptor can contain one or more additions, deletions, or substitutions of natural or non-natural amino acids relative to the naturally-occurring polypeptide sequence, so long as the receptor retains PK receptor signaling activity in response to PK. Such a modification can be, for example, a conservative change, wherein a substituted amino acid has similar structural or chemical properties, for example, substitution of an apolar amino acid with another apolar amino acid, substitution fo a charged amino acid with another amino acid of similar charge, and the like. Such a modification can also be a non-conservative change, wherein a substituted amino acid has different but sufficiently similar structural or chemical properties so as to not adversely affect the desired biological activity. Further, a minor modification can be the substitution of an L-configuration amino acid with the corresponding D-configuration amino acid with a non-natural amino acid. In addition, a minor modification can be a chemical or enzymatic modification to the polypeptide, such as replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation.

To determine or confirm that a PK receptor antagonist has PK receptor antagonistic activity, a variety of well-known assays can be employed. Such assays include both PK receptor signaling assays and ligand binding assays.

Signaling assays to identify or confirm the activity of PK receptor antagonists are known in the art. Because PK receptors are Gαq-coupled receptors, signaling assays typically used with other Gαq-coupled GPCRs can be used to determine PK receptor signaling activity. Gαq-coupled GPCRs, when bound to ligand, activate phospholipase C (PLC), which cleaves the lipid phosphatidylinositol 4,5-bisphosphate (PIP2) to generate the second messengers inositol 1,4,5-trisphosphate (IP3) and diacylglycerol (DAG). These second messengers increase intracellular $Ca^{2+}$ concentration and activate the MAP kinase cascade. The change in activity of PLC, or in abundance of downstream messengers, is a reflection of GPCR activation.

The specificity of Gα subunits for cell-surface receptors is determined by the C-terminal five amino acids of the Gα. Thus, if it is desired to assay a GPCR signaling pathway other than a typical Gαq pathway, a chimeric Gα containing the five C-terminal residues of Gαq and the remainder of the protein corresponding to another Gα can be expressed in a cell such that the PK receptor is coupled to a different signaling pathway (see, for example, Conklin et al., *Nature* 363:274–276 (1993), and Komatsuzaki et al., *FEBS Letters* 406:165–170 (1995)). For example, a PK receptor can be coupled to a Gαs or Gαi, and adenylate cyclase activation or inhibition assayed by methods known in the art.

Depending on the Gα and the assay system, GPCR signals that can be determined include, but are not limited to, calcium ion mobilization; increased or decreased production or liberation of arachidonic acid, acetylcholine, diacylglycerol, cGMP, cAMP, inositol phosphate and ions; altered cell membrane potential; GTP hydrolysis; influx or efflux of amino acids; increased or decreased phosphorylation of intracellular proteins; and activation of transcription of an endogenous gene or promoter-reporter construct downstream of any of the above-described second messenger pathways. An exemplary assay for PK receptor signaling in response to prokineticins is shown in Example I.

A variety of cell-based GPCR signaling assays, including assays performed in bacterial, yeast, baculovirus/insect systems and mammalian cells, are reviewed, for example, in Tate et al., *Trends in Biotech.* 14:426–430 (1996). More recently developed GPCR signaling assays include, for example, AequoScreen, which is a cellular aequorin-based functional assay that detects calcium mobilization (LePoul et al., *J. Biomol. Screen.* 7:57–65 (2002)); MAP kinase reporter assays (Rees et al., *J. Biomol. Screen.* 6:19–27 (2001); and fluorescence resonance energy transfer (FRET) based PLC activation assays (van der Wal, *J. Biol. Chem.* 276:15337–15344 (2001)). Several examples of PK receptor signaling assays are described in Lin et al., supra (2002) and in Masuda et al., supra (2002).

A PK receptor antagonist can be tested to determine whether it antagonizes PK binding to a PK receptor using a variety of well-known assays. Competitive and non-competitive binding assays for detecting ligand binding to a receptor are described, for example, in Mellentin-Micelotti et al., *Anal. Biochem.* 272:182–190 (1999); Zuck et al., *Proc. Natl. Acad. Sci. USA* 96:11122–11127 (1999); and Zhang et al., *Anal. Biochem.* 268;134–142 (1999). Examples of PK receptor binding assays are described in Lin et al., supra (2002) and in Masuda et al., supra (2002).

Depending on the assay selected for identifying or confirming PK receptor antagonist activity, the skilled person can determine an appropriate form for the PK receptor, such as in a live animal, a tissue, a tissue extract, a cell, a cell extract, or in substantially purified form. For example, for confirming the antagonistic activity of a PR receptor antagonist in receptor binding or signaling assays, the PK receptor will typically be either endogenously expressed or recombinantly expressed at the surface of a cell.

Figure 5:
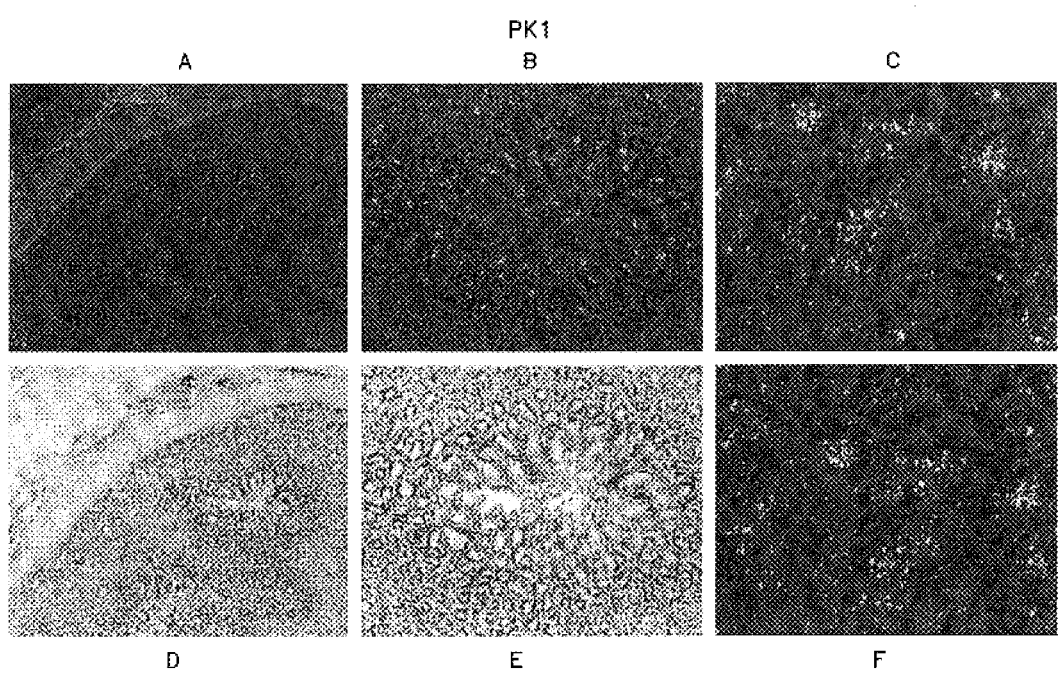
FIGS. 5A–F show expression of prokineticin 1 in mouse stomach.
Figure 6:
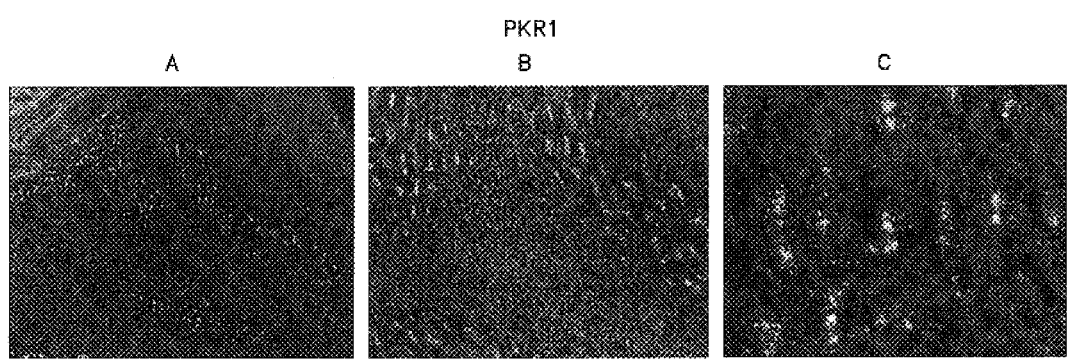
FIGS. 6A–C show expression of prokineticin 1 receptor (PKR1) in mouse stomach.

Cells that endogenously express a PK receptor are well known in the art, and include cells of the stomach as shown in FIGS. 5 and 6, as well as M2A7 melanoma cells (available from American Type Culture Collection as ATCC CRL-2500), M2 melanoma cells (Cunningham et al., *Science* 255;325–327 (1992)) and RC-4B/C pituitary tumor cells (ATCC CRL-1903)(see US 20020115610A1). Other cells that endogenously express a PK receptor include, for example, ideal and other gastrointestinal cells (see US 20020115610A1), endothelial cells such as BACE cells (Masuda et al., supra (2002)) and endothelial cells from adrenal cortex, choroid plexus, aorta, umbilical vein, brain capillary, microvessels of endocrine pancreas and dermal microvasculature; endocrine cells (Lin et al., supra (2002)), neural stem and progenitor cells, including cells in the subventricular zone of the lateral ventricle, the olfactory bulb/olfactory ventricle, the dentate gyrus of the hippocampus, and the inner nuclear layer of the retina.

The methods of the invention involve administering an amount of a PK receptor antagonist effective to modulate one or more indicia of gastric acid or pepsinogen secretion. As used herein, the term "gastric acid secretion" means the process of release of hydrochloric acid from parietal cells into the lumen of the stomach. As used herein, the term "pepsinogen secretion" means the process of release of pepsinogen from mucous cells and chief cells-into gastric juice.

As used herein, the term "effective" when used in reference to an amount of a PK receptor antagonist used to alter one or more indicia of gastric acid or pepsinogen secretion, means an amount of a PK receptor antagonist sufficient to alter a read-out corresponding to a particular index of gastric acid or pepsinogen secretion by at least about 10%, such as at least 25%, 50%, 2-fold, 5-fold, 10-fold, 50-fold, 100-fold or more, in comparison to a control.

As used herein, the term "modulating" means causing an alteration in the amount of gastric acid or pepsinogen secretion compared to a control level of gastric acid or pepsinogen secretion. Such alterations include an increase or decrease in the rate, duration or amount of secreted gastric acid or pepsinogen, or in an index of gastric acid or pepsinogen secretion. As used herein the term "index" or "indicia" when used in reference to gastric acid or pepsinogen secretion means an observable sign or indication of gastric acid or pepsinogen secretion. An index of gastric acid or pepsinogen secretion can be observed in a cell, tissue or animal because output of acid or pepsinogen and cellular changes consequent to output of acid can be observed in acid- or pepsinogen-secreting cells as well as in cells exposed to secreted acid and pepsinogen, which can be contained in a tissue. Exemplary indicia of gastric acid or pepsinogen secretion include reduced development of acid-related damage, such as reduced development of stress-induced gastric lesions, for example, water immersion-induced or restraint-induced gastric lesions; reduced gastric lesions, such as reduced aspirin-induced gastric lesions, reduced dimaprit-stimulated gastric lesions, reduced nonsteroidal antiinflammatory drug-induced gastric lesions, reduced cysteamine-induced gastric lesions, reduced methacholine-induced gastric lesions, reduced formation or severity of reflux esophagitis, reduced formation or severity of one or more ulcers of the gastrointestinal tract, reduced ethanol-induced gastric lesions reduced volume of gastric juice, reduced acid-induced abdominal pain, and the like. Gastric lesions can be located in any section of the gastrointestinal tract, including, for example, the duodenum, esophagus, and stomach.

In vitro assays for assessing an index of gastric acid or pepsinogen secretion include determining acid or pepsinogen release from perietal and peptic cells (Soll, *Am. J. Physiol* 238: G366–G375 (1980); Sol and Walsh, *Annu. Rev. Physiol.* 41:35–53(1979); Lavezzo et al., *Int J Tissue React* 6(2):155–165 (1984)) and in isolated gastric mucosae (Rangachari, *Am. J. Physiol.* 236:E733–E737 (1979), Bunce et al. *Br. J. Pharmacol* 58:149–156 (1976); and Lavezzo et al., *Int J Tissue React* 6(2):155–165 (1984)).

In vivo assays for assessing an index of gastric acid or pepsinogen secretion include a variety of well-known animals susceptible to developing acid-related gastrointestinal damage, including a variety of animal models in which acid secretion is routinely determined, and humans. Such models can vary based on a variety of parameters, such as the selected animal; whether gastric acid or pepsinogen secretion is basal or stimulated, and if stimulated, based on the type of stimulation, such as simulation of acid secretion by pentagastrin, histamine, insulin, food and sham feeding; and the administration route of the PK receptor antagonist used. The level of pepsin, the cleavage product of pepsinogen formed when pepsinogen is exposed to gastric acid, in gastric juice can be determined using well known methods, such as those described in Howden et al., *Aliment Pharmacol Ther* 1(4):305–315 (1987). Acid levels can be determined using well known methods, such as those described in Hirschowitz et al. *J. Pharmacol Exp Ther* 224(2):341–5 (1983), Wilson et al. *Gig Dis Sci* 29(9):797–801 (1984).

Exemplary animal models used for determining gastric acid and pepsinogen secretion include mammals with gastric fistulae, Heidenhain pouches and Thomas duodenal fistulae (see, for example, Magge et al. *J. Auton Pharmacol* 9(2): 129–137 (1989); Hirschowitz et al. *J. Pharmacology and Experimental Therapeutics* 224(2):341–345 (1983)). Specific examples of well known animal models for assessing effects of acid and pepsinogen secretion include gastric-fistula cats, stomach-lumen perfused rats (Lavezzo et al., *Int. J. Tiss Reac* VI (2):155–165 (1984); gastric fistula dogs (Hirschowitz et al., supra, 1983); and chronic gastric fistula rats (Kinoshita et al., *European Journal of Pharmacology* 321:325–332 (1997)). Normal animals, including humans, also can be used for determining gastric acid and pepsinogen secretion (see, for example, Howden et al., *Br J Clin Pharmacol* 20(2):137–139 (1985) and Dobrilla et al. *Ital J. Gastroenterol* 23(2):100–106 (1991)).

Any of the above-described in vitro and in vivo assays for determining the ability of a PK receptor antagonist to modulate gastric acid or pepsinogen secretion can involve comparison of a test sample, which can be, for example, a cell, tissue, or animal, to a control. One type of a "control" is a sample that is treated identically to the test sample, except the control is not exposed to the PK receptor antagonist. Another type of "control" is a sample that is similar to the test sample, except that the control sample does not express a PK receptor, or has been modified so as not to respond to a PK.

A method of the invention can be used in vitro, or in vivo to determine of the ability of a PK receptor antagonist to modulate gastric acid or pepsinogen secretion; to determine a therapeutically effective dosage; and can be used in vivo for a desired therapeutic effect. For in vitro testing in cells and tissues, any cell or tissue expressing a PK receptor and capable of producing an index of gastric acid or pepsinogen secretion can be used. Exemplary tissues and cells include gastric gland preparations and cells therefrom. For in vivo testing, any cell, tissue or animal model system containing a PK receptor and capable of producing an observable index of gastric acid or pepsinogen secretion known in the art can be used. For example, the method can be practiced in a suitable animal model system prior to testing in humans. Such model systems include, but not limited to, rats, mice, chicken, cows, dogs, cats, monkeys, rabbits, guinea pigs and the like.

The methods of the invention can involve administering a PK receptor antagonist to prevent or treat a variety of disorders characterized by acid-related gastrointestinal damage. As used herein, the term "administering" when used in reference to a PK receptor antagonist means providing to or contacting a cell, tissue or animal with the PK receptor antagonist. The term encompasses administering a PK receptor antagonist in vitro, as to a cell or tissue, which can be a cell or tissue removed from an animal or a cell or tissue placed in or adapted to culture; as well as in vivo, as to an animal. Modes of administering a PK receptor antagonist are described in detail herein below. As used herein, the term "acid-related gastrointestinal damage" when used in reference to a disease means a condition in which the process of gastric acid secretion sustains or augments a pathological condition. Exemplary types of acid-related gastrointestinal damage include irritation, inflammation and ulcer of gastrointestinal tissues.

A PK receptor antagonist used in a method of the invention for modulating gastric acid or pepsinogen secretion can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate formulation for a particular therapeutic application in humans can be determined, for example, based on the activity of the compound in the in vivo and in vitro assays described herein.

The therapeutically effective dosage for reducing or preventing gastric acid or pepsinogen secretion to reduce, prevent, or treat, for example, acid-related gastrointestinal damage, in vivo can be extrapolated from in vitro assays using a PK receptor antagonist, or a combination of a PK receptor antagonist with other gastric acid or pepsinogen secretion inhibiting factors. The effective dosage is also dependent on the method and means of delivery. Those skilled in the art will be able to determine an appropriate route of delivery of a PK receptor antagonist to be used in the methods of the invention for modulating gastric acid or pepsinogen secretion.

The total amount of a PK receptor antagonist can be administered as a single dose or by infusion over a relatively short period of time, or can be administered in multiple doses administered over a more prolonged period of time. Additionally, the compound can be administered in a slow-release matrix, which can be implanted for systemic delivery at or near the site of the target tissue. Contemplated matrices useful for controlled release of compounds, including therapeutic compounds, are well known in the art, and include materials such as DepoFoam™, biopolymers, micropumps, and the like.

A PK receptor antagonist can be administered to an animal by a variety of routes known in the art including, for example, intragastrically, intracerebrally, intraspinally, intravenously, intramuscularly, subcutaneously, intraorbitally, intracapsularly, intraperitoneally, intracisternally, intra-articularly, orally, intravaginally, rectally, topically, intranasally, or transdermally.

Generally, a PK receptor antagonist can be administered to an animal as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or detrains; antioxidants, such as ascorbic acid or glutathione; chelating agents; and low molecular weight proteins (see for example, "Remington's Pharmaceutical Sciences" 18th ed., Mack Publishing Co. (1990)).

For applications that require the compounds to cross the blood-brain barrier, or to cross cell membranes, formulations that increase the lipophilicity of the compound can be useful. For example, the compounds of the invention can be incorporated into liposomes (Gregoriadis, *Liposome Technology*, Vols. I to III, 2nd ed. (CRC Press, Boca Raton Fla. (1993)). Liposomes, which can contain phospholipids or other lipids, are generally nontoxic, physiologically acceptable and metabolizable carriers that are relatively simple to make and administer. Other approaches for formulating a compound such that it crosses the blood-brain barrier are known in the art and include the use of nanoparticles, which are solid colloidal particles ranging in size from 1 to 1000 nm (Lockman et al., *Drug Dev. Ind. Pharm.* 28:1–13 (2002)), and peptides and peptidomimetics that serve as transport vectors (Pardridge, *Nat. Rev. Drug Discov.* 1:131–139 (2002).

For applications in which is it desirable to administer a PK receptor antagonist locally to the area in need of treatment, a PK receptor antagonist can be provided, for example, by local infusion during surgery; topical application, such as in conjunction with a wound dressing after surgery; by injection; by means of a catheter; by means of a suppository; and by means of an implant, such as a porous, non-porous, or gelatinous material, including membranes, such as sialastic membranes, or fibers. For topical application, a PK receptor antagonist can be combined with a carrier, such as, for example, an ointment, cream, gel, paste, foam, aerosol, suppository, pad or gelled stick.

For oral administration applications, a PK receptor antagonist can be formulated in tablet or capsule form, which can contain, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. Suppositories generally contain active ingredient in the range of 0.5% to 10% by weight; oral formulations generally contain 10% to 95% active ingredient.

To enhance the modulation of gastric acid or pepsinogen secretion, more than one therapeutic approach or composition can be provided to an individual. For example, PK receptor antagonist that modulates gastric acid or pepsinogen secretion can be used in conjunction with conventional therapies for the disorder or condition being treated. As a non-limiting example, for treating ulcer, a PK receptor antagonist can be administered either alone or in conjunction with another antisecretory agent. Exemplary therapies with which PK receptor antagonist administration can be combined include histamine receptor 2 antagonists, such as cimetidine, tiotidine, ranitidine, CM57755, prostaglandins and prostaglandin analogues, such as FCE 20700, and proton pump inhibitors, such as T-330.

A PK receptor antagonist can also be used in a formulation together with other active ingredients, for example, for the treatment or prophylaxis of conditions involving infection by *Helicobacter pylori* of human gastric mucosa. Such other active ingredients may be antimicrobial agents, such as beta lactam antibiotics such as amoxicillin, ampicillin, cephalothin, cefaclor or cefixime; macrolides such as erythromycin, or clarithromycin; tetracyclines such as tetracycline or doxycycline; aminoglycosides such as gentamycin, kanamycin or amikacin; quinolones such as norfloxacin, ciprofloxacin or enoxacin; others such as metronidazole, nitrofurantoin or chloramphenicol; or preparations containing bismuth salts such as bismuth subcitrate, bismuth subsalicylate, bismuth subcarbonate, bismuth subnitrate or bismuth subgallate.

Based on this determination of an important pharmacological role of PR1 and PK2 receptors in control of gastric acid or pepsinogen secretion, the present invention provides methods of screening to identify compounds that modulate gastric acid or pepsinogen secretion, for example by modulating PK1 or PK2 receptor activity. Exemplary compounds that modulate PK2 receptor activity are PK2 receptor antagonist and agonists. Compounds identified using the methods of the invention can be used to modulate gastric acid or pepsinogen secretion for the treatment of a variety of gastrological disorders, and other conditions in which it is desired to modulate gastric acid or pepsinogen secretion, as described above.

Therefore, the invention provides a method for screening for a compound for modulating gastric acid or pepsinogen secretion in a mammal. The method involves (a) providing a compound that is a prokineticin (PK) receptor antagonist or agonist; and (b) determining the ability of the compound to modulate one or more indicia of gastric acid or pepsinogen secretion, wherein a compound that modulates the one or more indicia is identified as a compound for modulating gastric acid or pepsinogen secretion.

A PK2 receptor antagonist can be identified, for example, by contacting a PK receptor, such as PK1 or PK2 receptor, with one or more candidate compounds under conditions wherein PK promotes a predetermined signal and identifying a compound that reduces the predetermined signal. A PK receptor antagonist also can be identified by contacting a PK receptor, such as PK1 or PK2 receptor, with one or more candidate compounds in the presence of a receptor agonist under conditions wherein the agonist binds to the selected receptor and identifying a compound that reduces binding.

Similarly, a PK receptor agonist can be identified, for example, by contacting a PK receptor, such as PK1 or PK2 receptor, with one or more candidate compounds under conditions wherein PK promotes a predetermined signal and identifying a compound that promotes the predetermined signal. A PK receptor agonist can also be identified by contacting a PK receptor, such as PR1 receptor or PK2 receptor, with one or more candidate compounds under conditions wherein PK binds to a selected receptor and identifying a compound that binds to and activates the selected receptor.

The methods of the invention for screening for a compound that modulates gastric acid or pepsinogen secretion involves providing a PK receptor antagonist or agonist. The PK receptor antagonist or agonist can be provided to a cell preparation, tissue, organ, organism or animal that has at least one observable index of gastric acid or pepsinogen secretion and expresses a PK receptor. The ability of the PK receptor antagonist or agonist to modulate gastric acid or pepsinogen can be tested in a variety of animal species that exhibit indicia of gastric acid or pepsinogen secretion, as well as organs, tissues, and cells obtained from such animals, and cell preparations derived therefrom. The provided PK receptor antagonist or agonist can be a known PK receptor antagonist or agonist, such as PK2, PK1 or a PK2/PK1 chimera, or can be a compound identified as a PK receptor antagonist or agonist using in vitro screening methods described herein.

A variety of in vitro screening methods are useful for identifying a PK receptor antagonist or agonist to be provided in the methods of the invention for identifying a compound that modulates circadian rhythm. The ability of a compound to modulate PK receptor can be indicated, for example, by the ability of the compound to bind to and activate PK receptor, block agonist binding to PK receptor, promote a predetermined signal produced by a PK receptor, or reduce a predetermined signal produced by a PK receptor. Therefore, signaling and binding assays can be used to identify a PK receptor antagonist or agonist that is provided in the methods of the invention for identifying a compound that modulates gastric acid or pepsinogen secretion.

A signaling or binding assay used to identify a PK receptor antagonist or agonist. Because of the homology between PK2 and PK1 receptors, which have amino acid sequences that are about 85% identical, a PK2 receptor or PK1 receptor can be used in screening assays to identify a PK2 receptor agonist. Specifically, due to the homology between the PK1 receptor and PK2 receptor, a PK1 receptor agonist or antagonist is likely to also function as a PK2 receptor agonist or antagonist. Similarly, either PK1 or PK2 can function as an agonist in signaling and binding assay formats that employ a competitive agonist.

When a signaling assay is used to identify a PK receptor antagonist or agonist, the methods of the invention can involve contacting a PK1 receptor or PK2 receptor with one or more candidate compounds under conditions in which PK2 promotes a predetermined signal and identifying a compound that either decreases or increases the predetermined signal, respectively. When a binding assay is used to identify a PK receptor antagonist or agonist, the methods of the invention can involve contacting an PK1 receptor or PK2 receptor with one or more candidate compounds under conditions in which PK2 binds to the PK2 receptor and identifying a compound that either decreases binding of a PK2 receptor agonist to the PK1 receptor or PK2 receptor, or binds to and activates the PK1 receptor or PK2 receptor, respectively.

A PK2 receptor used in the screening methods of the invention can be, for example, a mouse or human PK2 receptor, including a recombinantly produced receptor or naturally occurring receptor present in a cell preparation. As used herein, the term "mouse PK2 receptor" is intended to mean a heptahelical membrane-spanning G-protein-coupled receptor comprising the amino acid sequence of mouse PK2 receptor, or a naturally-occurring or man-made minor modification thereof that binds to PK2 and signals through a G-protein coupled signal transduction pathway in response to PK2. A PK2 receptor also can bind to PK1 to induce PK2 receptor signaling. The invention provides a mouse PK2 receptor, which has the amino acid sequence referenced as SEQ ID NO:26.

Similarly, a PK1 receptor used in the screening methods of the invention can be, for example, a mouse or human PK1 receptor, including a recombinantly produced receptor or naturally occurring receptor present in a cell preparation. As used herein, the term "mouse PK1 receptor" is intended to mean a heptahelical membrane-spanning G-protein-coupled receptor comprising the amino acid sequence of mouse PK1 receptor, or a naturally-occurring or man-made minor modification thereof that binds to PK1 or PK2 and signals through a G-protein coupled signal transduction pathway in response to PK1 or PK2. An exemplary mouse PK1 receptor has the amino acid sequence referenced as SEQ ID NO:27.

For use in a screening assay, a minor modification of a PK receptor, such as the sequence referenced as SEQ ID NO:26 or 27, can have one or more additions, deletions, or substitutions of natural or non-natural amino acids relative to the native polypeptide sequence. Such a modification can be, for example, a conservative change, wherein a substituted amino acid has similar structural or chemical properties, for example, substitution of an apolar amino acid with another apolar amino acid (such as replacement of leucine with isoleucine). Such a modification can also be a nonconservative change, wherein a substituted amino acid has different but sufficiently similar structural or chemical properties so as to not adversely affect the desired biological activity, such as, replacement of an amino acid with an uncharged polar R group with an amino acid with an apolar R group (such as replacement of glycine with tryptophan). Further, a minor modification of the mouse PK2 receptor amino acid sequence referenced as SEQ ID NO:2 or 4 can be the substitution of an L-configuration amino acid with the corresponding D-configuration amino acid with a non-natural amino acid. In addition, a minor modification can be a chemical or enzymatic modification to the polypeptide, such as replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation.

Those skilled in the art can determine whether minor modifications to a PK receptor, such as the native mouse PK2 receptor sequence or PK1 receptor sequence, are advantageous for a screening assay. Such modifications can be made, for example, to enhance the stability, bioactivity of the mouse PK2 receptor or PK1 receptor. A PK receptor polypeptide can be prepared, for example, by recombinant methods, by synthetic methods, by post-synthesis chemical or enzymatic methods, or by a combination of these methods, and tested for ability to bind PK2 or PK1 or signal through a G-protein coupled signal transduction pathway.

Those skilled in the art also can determine regions in a PK receptor, such as a mouse PK2 receptor or PK1 receptor amino acid sequence, that can be modified without abolishing PK2 binding or signaling through a G-protein coupled signal transduction pathway. Structural and sequence information can be used to determine the amino acid residues important for PK2 receptor or PK1 receptor activity. For example, comparisons of amino acid sequences of PK2 receptor or PK1 receptor sequences from different species can provide guidance in determining amino acid residues that can be altered without abolishing activity.

Further, a large number of published GPCR structure-function studies have indicated regions of GPCRs involved in ligand interaction, G-protein coupling and in forming transmembrane regions, and indicate regions of GPCRs tolerant to modification (see, for example, Burstein et al., *J. Biol. Chem.*, 273(38):24322–7 (1998) and Burstein et al., *Biochemistry*, 37(12):4052–8 (1998)). In addition, computer programs known in the art can be used to determine which amino acid residues of a GPCR, such as a mouse PK2 receptor, can be modified as described above without abolishing activity (see, for example, Eroshkin et al., *Comput. Appl. Biosci.* 9:491–497 (1993)).

As used herein, the term "predetermined signal" is intended to mean a readout, detectable by any analytical means, that is a qualitative or quantitative indication of activation of G-protein-dependent signal transduction through PK receptor. Assays used to determine such qualitative or quantitative activation of G-protein-dependent signal transduction through PK2 receptor, are referred to below as "signaling assays." G-proteins, or heterotrimeric GTP binding proteins, are signal transducing polypeptides having subunits designated Gα, Gβ and Gγ, that couple to seven-transmembrane cell surface receptors. G-proteins couple to such receptors to transduce a variety of extracellular stimuli, including light, neurotransmitters, hormones and odorants to various intracellular effector proteins. G-proteins are present in both eukaryotic and prokaryotic organisms, including mammals, other vertebrates, flies and yeast.

A signaling assay can be performed to determine whether a candidate compound is a PK receptor agonist or antagonist. In such an assay, a PK receptor is contacted with one or more candidate compounds under conditions wherein the PK receptor produces a predetermined signal in response to a PK agonist, such as PK1 or PK2. In response to PK receptor activation, a predetermined signal can increase or a decrease from an unstimulated PK receptor baseline signal. A predetermined signal is an increasing signal, for example, when the amount of detected second messenger molecule is increased in response to PK receptor activation. A predetermined signal is a decreasing signal, for example, when the detected second messenger molecule is destroyed, for example, by hydrolysis, in response to PK receptor activation. A predetermined signal in response PK receptor activation can therefore be an increase in a predetermined signal that correlates with increased PK receptor activity, or a decrease in a predetermined signal that correlates with increased PK receptor activity. Accordingly, a PK receptor signaling assay of can be used to identify a PK receptor agonist that promotes production of a predetermined signal, whether the agonist promotes an increase in a predetermined signal that positively correlates with PK receptor activity, or a decrease in a predetermined signal that negatively correlates with PK receptor activity. Similarly, a signaling assay can be performed to determine whether a candidate compound is a PK receptor antagonist. In such a signaling assay, a PK receptor is contacted with one or more candidate compounds under conditions wherein the PK receptor produces a predetermined signal in response to a PK receptor agonist, such as PK, and a compound is identified that reduces production of the predetermined signal.

As also described above, signaling through G proteins can lead to increased or decreased production or liberation of second messengers, including, for example, arachidonic acid, acetylcholine, diacylglycerol, cGMP, cAMP, inositol phosphate, such as inositol-1,4,5-trisphosphate, and ions, including $Ca^{++}$ ions; altered cell membrane potential; GTP hydrolysis; influx or efflux of amino acids; increased or decreased phosphorylation of intracellular proteins; or activation of transcription.

Various assays, including high throughput automated screening assays, to identify alterations in G-protein coupled signal transduction pathways are well known in the art. Various screening assay that measure $Ca^{++}$, cAMP, voltage changes and gene expression are reviewed, for example, in Gonzalez et al., *Curr. Opin. in Biotech.* 9:624–631 (1998); Jayawickreme et al., *Curr. Opin. Biotech.* 8:629–634 (1997); and Coward et al., *Anal. Biochem.* 270:2424–248 (1999). Yeast cell-based bioassays for high-throughput screening of drug targets for G-protein coupled receptors are described, for example, in Pausch, *Trends in Biotech.* 15:487–494 (1997).

Assays to detect and measure G-protein-coupled signal transduction can involve first contacting a sample containing PK1 receptor or PK receptor, such as an isolated cell, membrane or artificial membrane, such as a liposome or micelle, with a detectable indicator. A detectable indicator can be any molecule that exhibits a detectable difference in a physical or chemical property in the presence of the substance being measured, such as a color change. Calcium indicators, pH indicators, and metal ion indicators, and assays for using these indicators to detect and measure selected signal transduction pathways are described, for example, in Haugland, *Molecular Probes Handbook of Fluorescent Probes and Research Chemicals*, Sets 20–23 and 25 (1992–94). For example, calcium indicators and their use are well known in the art, and include compounds like Fluo-3 AM, Fura-2, Indo-1, FURA RED, CALCIUM GREEN, CALCIUM ORANGE, CALCIUM CRIMSON, BTC, OREGON GREEN BAPTA, which are available from Molecular Probes, Inc., Eugene Oreg., and described, for example, in U.S. Pat. Nos. 5,453,517, 5,501,980 and 4,849,362.

Signaling through PK2 receptor and PK1 receptor promotes intracellular calcium ion mobilization, suggesting that these receptors normally couple to Gαq-containing G proteins. Therefore, signaling through the PK2 receptor or PK1 receptor can be detected by any assay known in the art that detects intracellular calcium ion mobilization. A calcium ion mobilization assay can be performed in the presence or absence of a PK1 or PK2.

If desired, a predetermined signal other than $Ca^{2+}$ influx can be used as the readout for PK2 receptor activation. The specificity of a G-protein for cell-surface receptors is determined by the C-terminal five amino acids of the Gα subunit. The nucleotide sequences and signal transduction pathways of different classes and subclasses of Gα subunits in a variety of eukaryotic and prokaryotic organisms are well known in the art. Thus, any convenient G-protein mediated signal transduction pathway can be assayed by preparing a chimeric Gα containing the C-terminal residues of a Gα that couples to PK2 receptor or PK1 receptor, such as Gαq, with the remainder of the protein corresponding to a Gα that couples to the signal transduction pathway it is desired to assay. Methods of recombinantly expressing chimeric Gα proteins are known in the art and are described, for example, in Conklin et al., *Nature* 363:274–276 (1993), Komatsuzaki et al., *FEBS Letters* 406:165–170 (1995), and Saito et al., *Nature* 400:265–269 (1999). Additionally, chimeric Gα proteins can be prepared by synthetic methods.

Another type of signaling assay involves determining changes in gene expression in response to a PK2 receptor or PK1 receptor agonist or antagonist. A variety of signal transduction pathways contribute to the regulation of transcription in animal cells by stimulating the interaction of transcription factors with genetic sequences termed response elements in the promoter regions of responsive genes. Assays for determining the interaction of transcription factors with promoter regions to stimulate gene expression are well known to those skilled in the art and are commercially available. A variety of promoters, including a PK2 promoter, can be employed in gene expression assays to detect PK2 receptor or PK1 receptor activity. Exemplary gene expression assays are those that involve transducing cells with a promoter-reporter nucleic acid construct such that a readily detectable protein such as β-lactamase, luciferase, green fluorescent protein or β-galactosidase will be expressed in response to contacting PK2 receptor or PK1 receptor with an agonist, such as PK2, PK1 or a PK2/PK1 chimera. Compounds identified in such gene expression assays can act either at the level of the cell surface, by modulating the activity of a PK2 receptor, the activity of a component of the PK2 receptor signal cascade or the activity of factors that modulate transcription of a PK2-controlled gene.

An assay to identify compounds that function as PK receptor agonists or antagonists is performed under conditions in which contacting the receptor with a known PK receptor agonist would produce a predetermined signal. If desired, the assay can be performed in the presence of a known PK receptor agonist, such as a PK2 or a PK1, including those referenced above, or a PK2/PK1 chimera, including those referenced as SEQ ID NOS:20 and 21. The agonist concentration can be within. 10-fold of the $EC_{50}$.

Thus, an agonist that competes with PK2, PK1 or a PK2/PK1 chimera, for signaling through the PK2 receptor, or indirectly potentiates the signaling activity of PK2, can be readily identified. Similarly, an agonist that competes with PK2, PK1 or a PK2/PK1 chimera for signaling through the PK1 receptor can be readily identified.

A binding assay can be performed to identify compounds that are PK receptor agonists or antagonists. In such an assay, a PK2 receptor or PK1 receptor can be contacted one or more candidate compounds under conditions in which PK1 or PK2 binds to the selected receptor and a compound that binds to the selected receptor or that reduces binding of an agonist to selected receptor can be identified. Contemplated binding assays can involve detectably labeling a candidate compound, or competing an unlabeled candidate compound with a detectably labeled PK agonist, such as a PK2, PK1 or PK2/PK1 chimera. A detectable label can be, for example, a radioisotope, fluorochrome, ferromagnetic substance, or luminescent substance. Exemplary radiolabels useful for labeling compounds include $^{125}I$, $^{14}C$ and $^{3}H$. Methods of detectably labeling organic molecules, either by incorporating labeled amino acids into the compound during synthesis, or by derivatizing the compound after synthesis, are known in the art.

In order to determine whether a candidate compound decreases binding of detectably labeled PK to PK receptor, the amount of binding of a given amount of the detectably labeled PK2 is determined in the absence of the candidate compound. Generally the amount of detectably labeled PK will be less than its $K_d$, for example, ⅟₁₀ of its $K_d$. Under the same conditions, the amount of binding of the detectably labeled PK2, PK1 or PK2/PK1 chimera in the presence of the candidate compound is determined. A decrease in binding due to a candidate compound characterized as a PK receptor ligand is evidenced by at least 2-fold less, such as at least 10-fold to at least 100-fold less, such as at least 1000-fold less, binding of detectably labeled PK2, PK1 or PK2/PK1 chimera to PK2 receptor in the presence of the candidate compound than in the absence of the candidate compound.

An exemplary assay for determining binding of detectably labeled PK2, PK1 or PK2/PK1 chimera to PK2 receptor or PK1 receptor is the radioligand filter binding assay described in Li et al. *Molecular Pharmacology* 59:692–698 (2001)). A variety of other low- and high-throughput assays suitable for detecting selective binding interactions between a receptor and a ligand are known in the art. Such assays include, for example, fluorescence correlation spectroscopy (FCS) and scintillation proximity assays (SPA) reviewed in Major, *J. Receptor and Signal Transduction Res.* 15:595–607 (1995); and in Sterrer et al., *J. Receptor and Signal Transduction Res.* 17:511–520 (1997)). Binding assays can be performed in any suitable assay format including, for example, cell preparations such as whole cells or membranes that contain PK2 receptor or PK1 receptor, or substantially purified PK2 receptor polypeptide or PK1 receptor, either in solution or bound to a solid support.

A detectably labeled PK2, PK1 and PK2/PK1 chimera can be useful in many of the in vitro assays described above. PK2, PK1 and PK2/PK1 chimeras can be derivatized with, or conjugated to, a moiety that is detectable by any analytical means. Such detectably labeled molecules useful in the assays disclosed herein generally retain their ability to bind PK2 receptor or PK1 receptor at subnanomolar concentrations. For example, a detectable moiety can be a radioisotope, fluorochrome, ferromagnetic substance, or luminescent substance. In one embodiment, the detectably labeled PK2, PK1 or PK2/PK1 chimera is radiolabeled. Exemplary radiolabels useful for labeling peptides include $^{125}$I, $^{14}$C and $^{3}$H. Methods of detectably labeling peptides, either by incorporating labeled amino acids into the peptide during synthesis, or by derivatizing the peptide after synthesis, are known in the art. As described in Li et al. supra (2001), an exemplary detectably labeled PK2, PK1 or PK2/PK1 chimera is human PK2, radioiodinated at the core Tyr with $^{125}$I, which binds membranes of cells transfected with PK1 receptor with an apparent $K_d$ of 70 pM.

Assay methods for identifying compounds that selectively bind to or modulate signaling through a PK2 receptor generally involve comparison to a control. One type of a "control" is a preparation that is treated identically to the test preparation, except the control is not exposed to the candidate compound. Another type of "control" is a preparation that is similar to the test preparation, except that the control preparation does not express the receptor, or has been modified so as not to respond selectively to a particular PK. In this situation, the response of the test preparation to a candidate compound is compared to the response (or lack of response) of the control preparation to the same compound under substantially the same reaction conditions.

Assays for determining an index of gastric acid or pepsinogen secretion are described above with respect to PK receptor antagonists. These methods and others well known in the art can be used in the screening methods for identifying a compound that is a PK receptor antagonist or agonist for modulating gastric acid or pepsinogen secretion in a mammal.

It is understood that modifications which do not substantially affect the activity of the various embodiments of this invention are also included within the definition of the invention provided herein. Accordingly, the following examples are intended to illustrate but not limit the present invention.

EXAMPLE I

Prokineticin Receptor Antagonists Reduce Prokineticin Receptor-Mediated Calcium Mobilization This example shows the ability prokineticin receptor antagonists to reduce prokineticin receptor 1 (PKR1)-mediated calcium mobilization and prokineticin receptor 2 (PKR2)-mediated calcium mobilization.

To determine whether various modified prokineticins (PKs) have the ability to modulate PK receptor function, the modified prokineticins were tested for their ability to function as agonists or antagonists in PK receptor-mediated calcium mobilization assays. Shown in Table 2 below are the structures of several of the modified prokineticins tested.

An aequorin-based luminescent assay for measuring mobilization of intracellular $Ca^{2+}$ was performed essentially as described in Liu et al., supra, (2002). Chinese hamster ovary (CHO) cells stably expressing photoprotein aequorin and hPKR1 or hPKR2 were used for this assay. Briefly, the cells was charged in Opti MEM containing 30 μM reduced glutathione and 8 μM of coelenterazine cp at 37° C. for 2 hours. The cells were then detached by typsinization, spun down, rinsed once with PBS, recentrifuged, resuspended and maintained in Hank's Balanced Salt Solution(HBSS) plus 10 mM HEPES(pH7.5) and 0.1% BSA at about $5\times10^5$ cells/ml. Measurements were recorded using a Monolight 2010 luminometer (Analytical Luminescence Laboratory).

For agonist assays, 100 ul of cells were injected into 20 ul of ligand, and luminescence was recorded for 15 seconds. For antagonist assays, 100 ul of cells were injected into a mixture of 20 ul antagonist and 100 ul PK1 or PK2 (10 nM), and luminescence was recorded for 15 seconds. For antagonist assays with preincubation, 100 ul of PK1 or PK2 (10 nM) was injected into a mixture of 20 ul antagonist and 100 ul cells, which were incubated at RT for 1 hour.

Figure 2A:
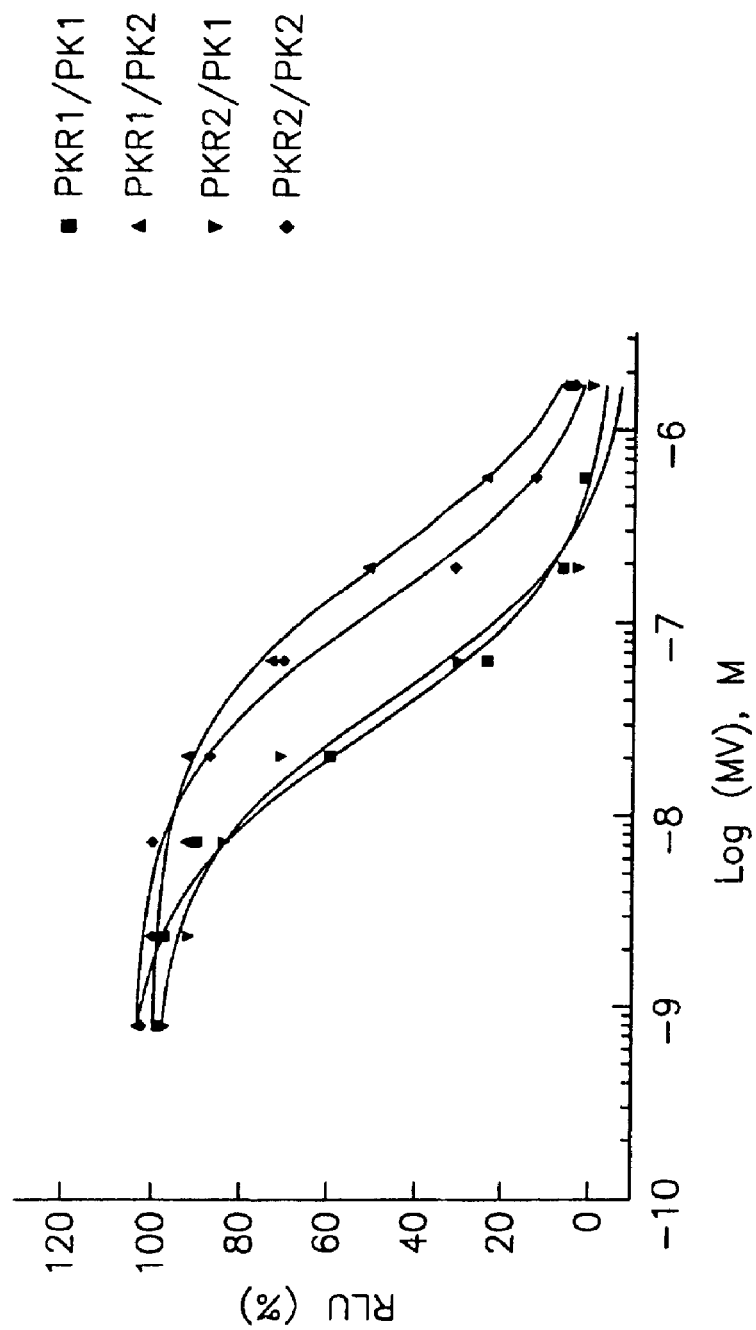
FIG. 2A shows a dose-response curve of PK receptor antagonist MV PK1 (SEQ ID NO:20) assayed for its ability to inhibit PKR1- and PKR2-mediated calcium mobilization in response to either PK1 or PK2.
Figure 2B:
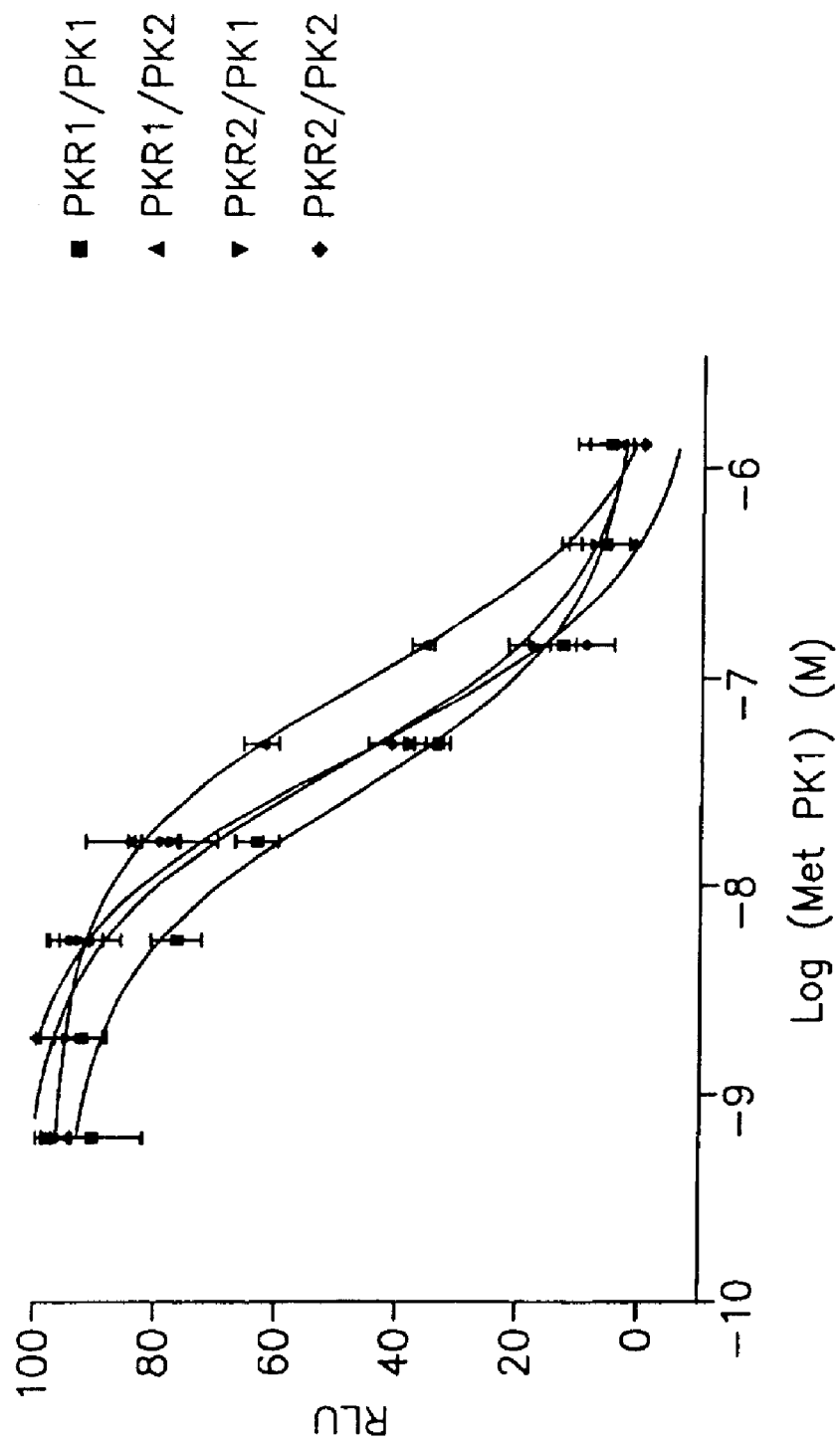
FIG. 2B shows a dose-response curve of PK receptor antagonist Met PK1 (SEQ ID NO:18) assayed for its ability to inhibit PKR1- and PKR2-mediated calcium mobilization in response to either PK1 or PK2.
Figure 2C:
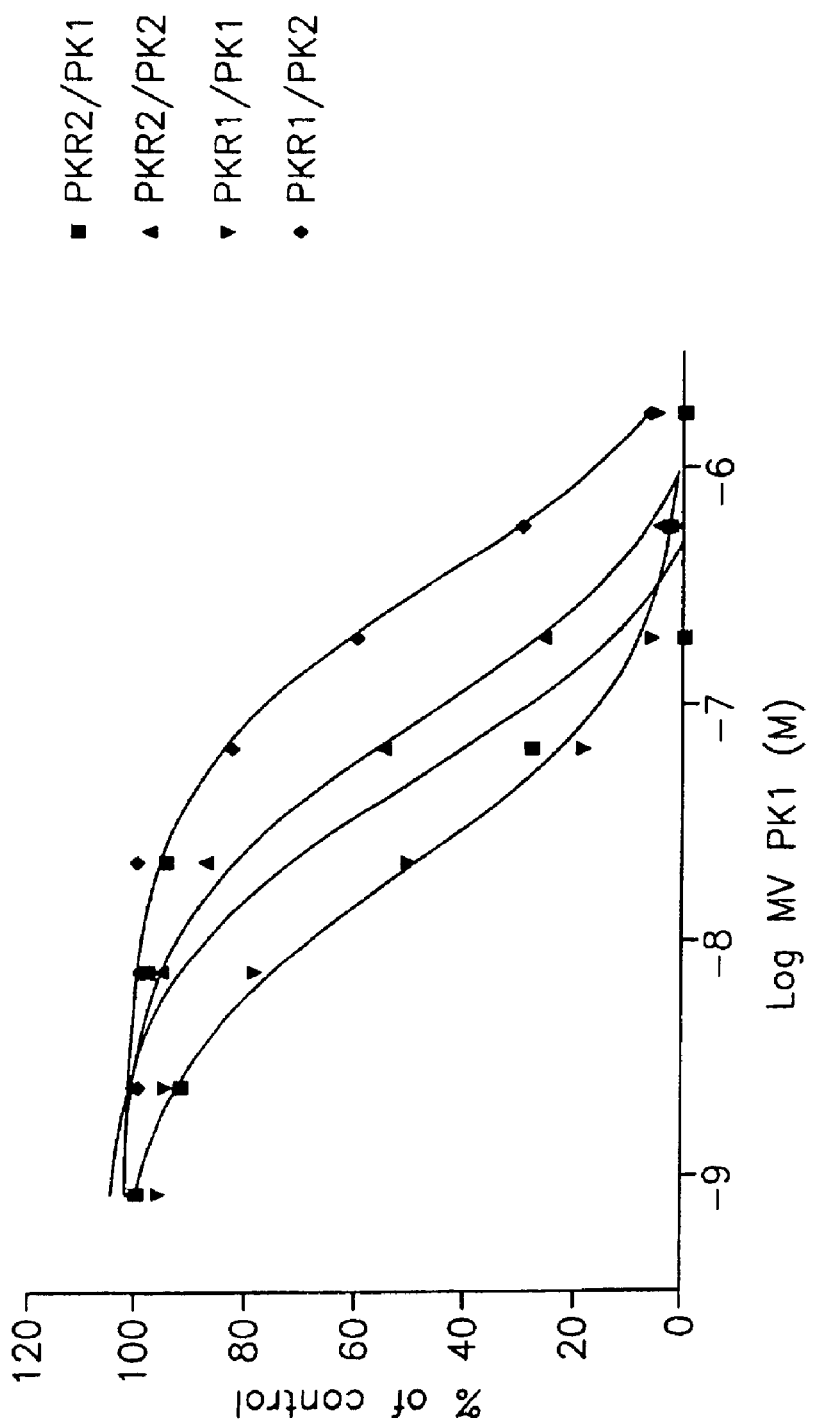
FIG. 2C shows a dose-response curve of PK receptor antagonist MV PK1 (SEQ ID NO:20) assayed for its ability to inhibit PKR1- and PKR2-mediated calcium mobilization in response to either PK1 or PK2.

FIG. 2A shows a dose-response curve of PK receptor antagonist MV PK1 (SEQ ID NO:20) assayed for its ability to inhibit PKR1- and PKR2-mediated calcium mobilization in response to either PK1 or PK2. FIG. 2B shows a dose-response curve of PK receptor antagonist Met PK1 (SEQ ID NO:18) assayed for its ability to inhibit PKR1- and PKR2-mediated calcium mobilization in response to either PK1 or PK2. FIG. 2C shows a dose-response curve of PK receptor antagonist MV PK1 (SEQ ID NO:20) assayed for its ability to inhibit PKR1- and PKR2-mediated calcium mobilization in response to either PK1 or PK2.

Figure 3:
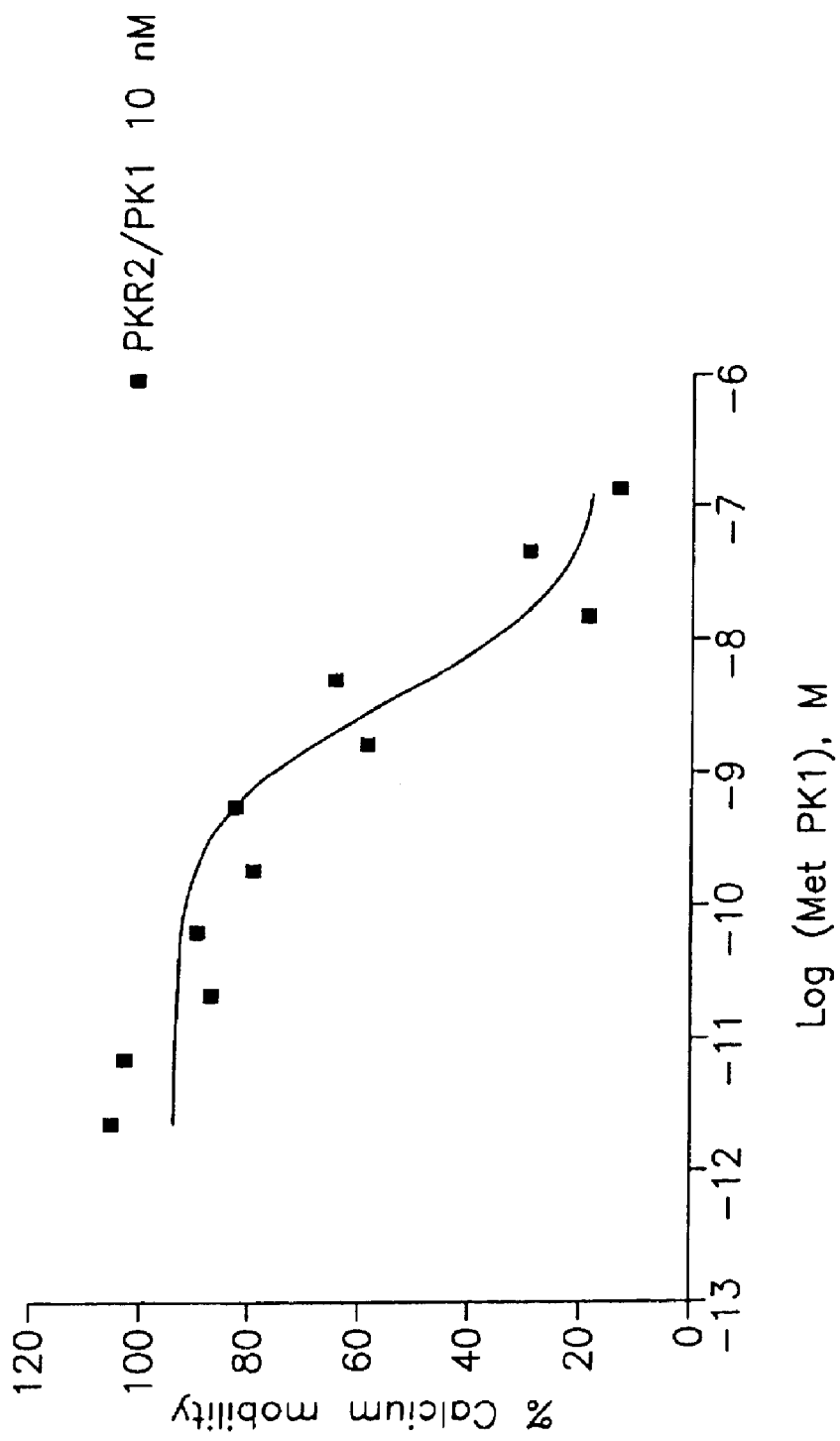
FIG. 3 shows a dose-response curve of PK receptor antagonist Met PK1 (SEQ ID NO:18) assayed for its ability to inhibit PKR2-mediated calcium mobilization in response to PK1 when the receptor is pretreated with Met PK1.

To determine whether pretreatment of a PK receptor with a modified prokineticin alters the ability of the modified prokineticin to modulate PK receptor function, Met PK1 was preincubated with receptor for 1 hour prior to stimulation of the receptor with ligand (PK1, 10 nM). FIG. 3 shows a dose-response curve of PK receptor antagonist Met PK1 (SEQ ID NO:18), which indicates that Met PK1 is more potent in antagonizing PK1 effect in a pretreatment regimen. The $IC_{50}$ for Met PK1 with pretreatment is 3.3 nM, whereas the $IC_{50}$ for Met PK1 in the absence of pretreatment is 36 nM.

Figure 4:
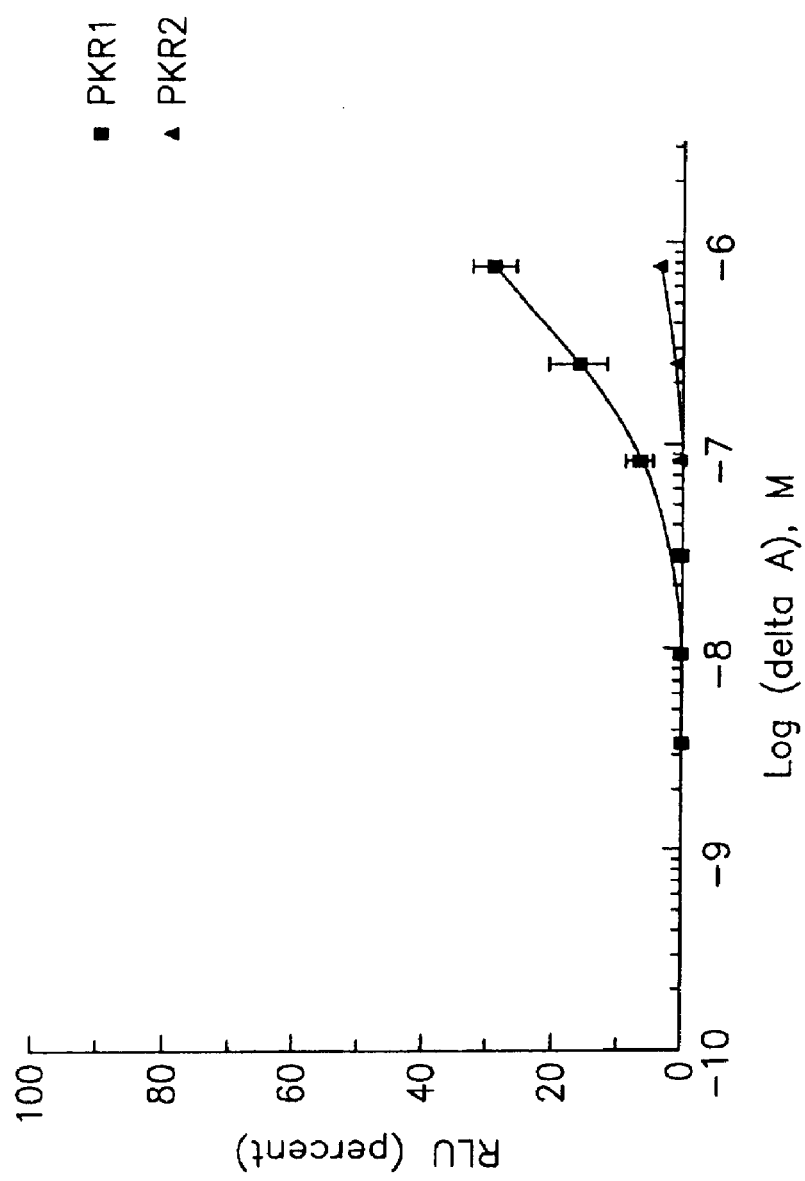
FIG. 4 shows a dose response curve of prokineticin receptor antagonist delA-PK1 (SEQ ID NO: 16) assayed for its ability to activate PKR1- and PKR2-mediated calcium mobilization.

FIG. 4 shows a dose response curve of prokineticin receptor antagonist delA-PK1 (SEQ ID NO: 16) assayed for its ability to activate PKR1- and PKR2-mediated calcium mobilization.

TABLE 2

Structures of Modified Prokineticins

| Name | Structure |
|---|---|
| Wild type | PK1 and 2K2 |
| Chimera 12 | AVITG-exon 2 of PK1-exon3 of PK2 |
| Chimera 21 | AVITG-exon2 of PK2-exon3 of PK1 |
| PK2-insert | Insertion of 23 amino acids between exon2 and exon 3 |
| C18S | Substitute cysteine 18 of PK1 with serine |
| C60R | Substitute cysteine 60 of PK1 with arginine |
| AVITG-colipase | Fuse AVITG to the N-terminus of colipase |
| AVITG-dickkopf | Fuse AVITG to the N-terminus of dickkopf |
| DelA | Delete the alanine 1 of PK1 |
| MV PK1 | Substitute alanine1 of PK1 with methionine |
| Met PK1 | Add a methionine to the N-terminus of PK1 |
| GIL-PK1 | Add a tripeptide Gly-Ile-Leu to the N-terminus of PK1 |
| AlaG | Mutate the N-terminal AVITGA of PK1 to AAAAAA |
| Peptide | AVITGACERDVQCG |

These data and other data obtained using similar methods show that (a) modified prokineticins C18S, C60R, AVITG-colipase, AVITG-dickkopf, MV PK1, Met PK1, and Ala6, lack detectable agonist activity, (b) modified prokineticin GIL-PK1 has weak agonist activity, (c) chimera 12 and 21 have agonist activity, (d) PK2-insert has partial agonist activity and (e) Met PK1 and MV PK1 have antagonist activity.

EXAMPLE II

Expression of PK1 and PK1 Receptor in Mouse Stomach

This example shows that prokineticin 1 (PK1) and PK1 receptor are expressed in mouse stomach.

Expression of PK1 mRNA in the fundic area of the mouse stomach was determined using in situ hybridization with a mouse PK1 probe (nucleotides 1 to 682 of GenBank accession number AF487281) on sections of adult mouse stomach. FIGS. 5A, B, C and F show dark field emulsion-dipped images of mouse stomach tissue. FIGS. 5D and E show Nissl-stained bright field images. Expression of PK1 mRNA is evidenced by the bright pattern of signal in gastric gland areas of the stomach tissue, as shown in Figures A, B, C and F.

Expression of PK1 receptor mRNA in the fundic area of mouse stomach was determined using in situ hybridization with a mouse PKR1 probe (nucleotides 1457 to 2556 of GenBank accession number AF487278) in sections of adult mouse stomach. Figures A, B and C are dark field emulsion-dipped images of mouse stomach tissue. Expression of PK1 receptor mRNA is evidenced by the bright pattern of signal in gastric gland areas of the stomach tissue, as shown in Figures A, B and C.

In situ hybridization was be carried out as follows. Organs were quickly removed from mice after cervical dislocation and frozen in isopentane at −20 degrees C. for 30 seconds. Twenty-micrometer coronal sections were cut on a cryostat and serial sections collected. Antisence riboprobes containing the coding region of mouse PK1 or the 3'UTR (untranslated region) of the mouse PKR1 were prepared. The 3'UTR of the PKR1 was used as PKR1 and PKR2 are over 80% identical at nucleic acid sequence level in their coding regions. These riboprobes were generated by T7 or SP6 RNA polymerases and radioactively labeled with $^{35}$S-UTP. Probes were used at concentration of $1\times10^7$ cpm/ml. Sections were pretreated with proteinase K, hybridized for 18 hours at 60 degrees C. followed by RNase digestion, high stringency washes and dehydration. Tissue sections were then be exposed to BioMax film (Kodak) for 3–4 days. The mRNA distributions were then analyzed in autoradiograms and emulsion-dipped sections. Autoradiographic images were captured using MCID and emulsion-dipped stomach images were taken under the transillumination microscope (BX50, Olympus) by using Spot camera software version 2.2.2 (Diagnostic Instruments, Sterling Heights, Mich.). Figures were prepared by using Adobe Photoshop (version 5.5).

Figure 7:
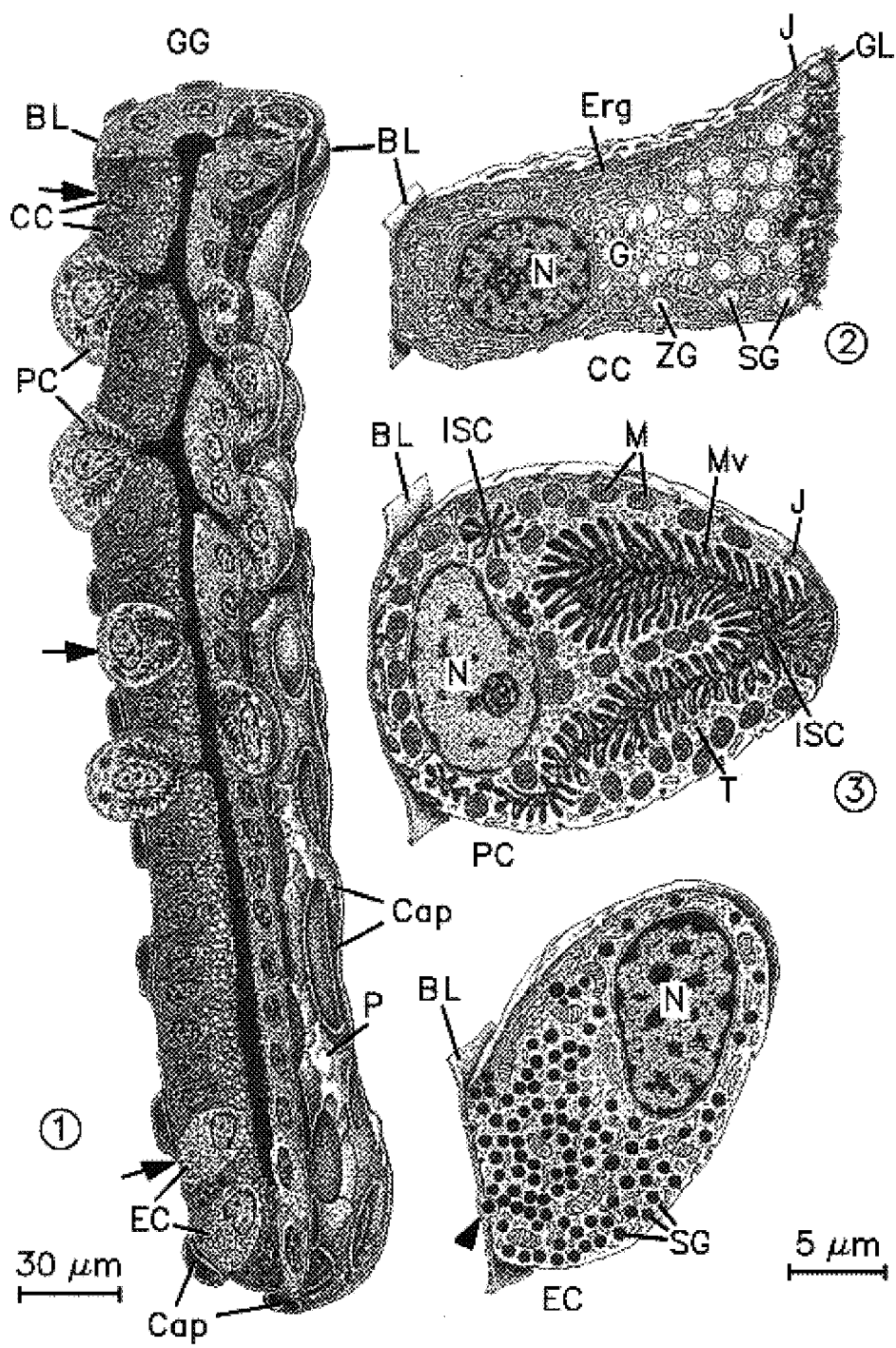
FIG. 7 shows a diagram of the human gastric gland.

A diagram of the gastric gland, found in the fundic area of the stomach is shown in FIG. 7. Indicated in the diagram are GG (gastric gland proper); PC (parietal cells); CC (chief cells); BL (basal lamina); EC (endochromaffin cells); P (pericytes); SG (secretory granules); ZG (Zymogen granules); Erg (ergastoplasm); ISC (intracellular secretory canaliculus); M (mitochondria); Mv (microvilli); and T (tubulovesicular profiles).

These data show that PK1 and PK1 receptor are expressed in the mouse stomach, and in particular, in the gastric gland of mouse stomach.

EXAMPLE III

Expression of PK1 and PK1 Receptor in Mouse Stomach

This example shows a method for an in vitro cell-based assay for determining the effect of modulating PK receptor on gastric acid or pepsinogen secretion.

Gastric glands for use in the in vitro assay are prepared by dispersing gastric glands from rabbit fundic mucosa according to the method of Berglindh and Öbrink, *Acta Physiol Scand.* 96(2):150–9(1976). Rabbit glands are obtained from New Zealand white rabbits (2–3 kg body weight), which are anesthetised with 50 mg/kg ketamine and 5 mg/kg xylazine. PBS is perfused under pressure through the gastric vasculature until the stomach doubles in volume; the stomach is then removed, rinsed in PBS and the fundus separated. The fundic tissue is placed on a warm surface while the serosa is removed and the mucosa scraped off the tunica muscularis and cut into small pieces. Mucosal tissue is incubated at 37° C. for 30 minutes in 50 ml collagenase solution while being gassed with 100% oxygen and gently shaken. Parietal cells are enriched by elutriation utilizing a Beckman JM6-C centrifuge with a JE-5.0 quick assembly rotor. The fraction of enriched parietal cells is separated from other cells by centrifugation in a Nycodenz (Nycomed, Oslo, Norway) step gradient. The band of parietal cells is harvested and diluted in culture medium (DMEM-Ham's F-12 medium containing 2 mg/ml BSA, 800 nM insulin, 5 µg/ml transferrin, 5 ng/ml sodium selenite, 10 nM hydrocortisone, 8 nM EGF, 5 µg/ml geneticin, 50 µg/ml novobiocin, 100 µg/ml gentamicin, 10 µg/ml phenol red) to 5000 cells/µl. Cells are cultured in 1.9 cm$^2$ culture dishes priorily coated with Matrigel (Becton Dickinson, Bedford, Mass.) in a humidified incubator at 37° C. in air.

To monitor the acid production of cultured rabbit parietal cells, an aminopyrine (AP) uptake assay is performed utilizing dimethylamine [$^{14}$C]-AP of 3.92 GBq/mol (Amersham). $^{14}$C-AP accumulation is measured using a modification of the methods of Berglindh et al. *Acta Physiol. Scand.* 97:401–414. (1976) and Sack and J. G. Spenney, *Am. J. Physiol.* 243: G313–G319 (1982). Parietal cells are incubated in oxygen-saturated buffer A (10 mM HEPES, pH 7.4, 114.4 mM NaCl, 5.4 mM KCl, 5 mM Na$_2$HPO$_4$, 1 mM NaH$_2$PO$_4$, 1.2 mM MgSO$_4$, 2 mM CaCl$_2$, 2 mg/ml BSA, 10 mM glucose, 0.5 mM DTT, 1 mM pyruvate) in the absence or presence of a PK receptor antagonist for 60 min. Concentration of recombinant PK receptor antagonists to be tested include 0.1, 0.3 1, 3, 10, 30, 100, 300, 1000 nM. Carbachol (0 to 10$^{-3}$ M; Sigma) serves as a positive control. Cells are washed twice in buffer A, lysed, and counted in a β-scintillation counter. The basal acid secretion is determined by inhibition of acid secretion with 10$^4$ M ranitidine (Sigma). Non-specific [$^{14}$C]-AP accumulation is determined using control assays in which H+secretion is blocked with omeprazol (10$^{-5}$ M; AstraZeneca).

Thus, an vitro assay can be used to determine the effect of PK receptor antagonists on gastric acid secretion.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A method of reducing gastric acid or pepsinogen secretion, comprising administering to an animal an amount of a prokineticin receptor antagonist effective to reduce one or more indicia of gastric acid or pepsinogen secretion, wherein said antagonist comprises an amino acid sequence having at least 80% identity to amino acids to 7 to 77 of SEQ ID NO: 3, said sequence comprising;
   (a) the 10 conserved cysteine residues of SEQ ID NO: 3, and
   (b) from 0 to 9 of amino acids 78 to 86 of SEQ ID NO: 3,
   wherein amino acids 1 to 6 preceeding that part of said antagonist having at least 80% identity to amino acids to 7 to 77 of SEQ ID NO: 3 do not consist of amino acids AVITGA (SEQ ID NO: 21).

2. The method of claim 1, wherein said antagonist comprises 6 or more amino acids N-terminal to the first conserved cysteine residue.

3. The method of claim 1, wherein said antagonist comprises 7 or more amino acids N-terminal to the first conserved cysteine residue.

4. The method of claim 3, wherein said 7 or more amino acids are MAVITGA (SEQ ID NO:23).

5. The method of claim 4, wherein said antagonist comprises SEQ ID NO:18.

6. The method of claim 5, wherein said antagonist consists of SEQ ID NO:18.

7. The method of claim 1, wherein said antagonist comprises SEQ ID NO:20.

8. The method of claim 1, wherein said antagonist consists of SEQ ID NO:20.

9. The method of claim 1, wherein said antagonist comprises 5 or fewer amino acids N-terminal to said first conserved cysteine residue.

10. The method of claim 9, wherein said 5 or fewer amino acids are VITGA (SEQ ID NO:22).

11. The method of claim 10, wherein said antagonist comprises SEQ ID NO:16.

12. The method of claim 11, wherein said antagonist consists of SEQ ID NO:16.

13. The method of claim 1, wherein amino acid residues that differ from residues 7 to 77 of SEQ ID NO:3 are conservative substitutions thereof.

14. The method of claim 1, wherein amino acid residues that differ from residues 7 to 77 of SEQ ID NO:3 consist of the corresponding residues from SEQ ID NO:6.

15. The method of claim 1, wherein said antagonist comprises amino acids 7 to 77 of SEQ ID NO:3.

16. The method of claim 1, wherein said one or more indicia of gastric acid or pepsinogen secretion comprises gastric lesion formation or severity.

17. The method of claim 1, wherein said one or more indicia of gastric acid or pepsinogen secretion comprises reduced ulcer formation or severity.

18. The method of claim 1, wherein said one or more indicia of gastric acid or pepsinogen secretion comprises reduced reflux esophagitis formation or severity.

19. The method of claim 1, wherein said antagonist is administered to a tissue in said animal.

20. The method of claim 1, wherein said animal is any of rat, cat, dog, non-human primate, and human.

21. The method of claim 1, wherein said antagonist is administered to an animal susceptible to developing acid-related gastrointestinal damage.

22. The method of claim 21, wherein said animal has a gastrointestinal cancer.

23. A method of reducing gastric acid secretion, comprising administering to an animal an amount of a prokineticin receptor antagonist effective to reduce one or more indicia of gastric acid secretion, wherein said antagonist comprises an amino acid sequence having at least 80% identity to amino acids to 7 to 77 of SEQ ID NO:6, said sequence comprising;
  (a) the 10 conserved cysteine residues of SEQ ID NO:6, and
  (b) from 0 to 4 of amino acids 78 to 81 of SEQ ID NO:6, wherein amino acids 1 to 6 preceeding that part of said antagonist having at leat 80% identity to amino acids to 7 to 77 of SEQ ID NO: 3 do not consist of amino acids AVITGA (SEQ ID NO:21).

24. The method of claim 23, wherein said antagonist comprises 6 or more amino acids N-terminal to the first conserved cysteine residue.

25. The method of claim 23, wherein said antagonist comprises 7 or more amino acids N-terminal to the first conserved cysteine residue.

26. The method of claim 25, wherein said 7 or more amino acids are MAVITGA (SEQ ID NO:23).

27. The method of claim 26, wherein said antagonist comprises SEQ ID NO:18.

28. The method of claim 23, wherein said antagonist comprises 5 or fewer amino acids N-terminal to said first conserved cysteine residue.

29. The method of claim 28, wherein said 5 or fewer amino acids are VITGA (SEQ ID NO:22).

30. The method of claim 23, wherein amino acid residues that differ from residues 7 to 77 of SEQ ID NO:6 are conservative substitutions thereof.

31. The method of claim 24, wherein amino acid residues that differ from residues 7 to 77 of SEQ ID NO:6 consist of the corresponding residues from SEQ ID NO:3.

32. The method of claim 31, wherein said antagonist comprises amino acids 7 to 77 of SEQ ID NO:6.

33. The method of claim 23, wherein said one or more indicia of gastric acid secretion comprises gastric lesion formation or severity.

34. The method of claim 23, wherein said one or more indicia of gastric acid secretion comprises reduced ulcer formation or severity.

35. The method of claim 23, wherein said one or more indicia of gastric acid secretion comprises reduced reflux esophagitis formation or severity.

36. The method of claim 23, wherein said antagonist is administered to a tissue in said animal.

37. The method of claim 23, wherein said animal is any of rat, cat, dog, non-human primate, and human.

38. The method of claim 23, wherein said antagonist is administered to an animal susceptible to developing acid-related gastrointestinal damage.

39. The method of claim 38, wherein said individual has a gastrointestinal cancer.

* * * * *